US010258323B2

(12) United States Patent
Lane et al.

(10) Patent No.: US 10,258,323 B2
(45) Date of Patent: Apr. 16, 2019

(54) APPARATUS AND METHOD FOR SUTURING TISSUE

(71) Applicant: SafePath Medical, Inc., Amesbury, MA (US)

(72) Inventors: Joseph P. Lane, Amesbury, MA (US); Michael W. Sutherland, Pelham, NH (US); Thomas D. Egan, Marblehead, MA (US); John DePiano, Burlington, MA (US)

(73) Assignee: SAFEPATH MEDICAL, INC., Amesbury, MA (US)

( * ) Notice: Subject to any disclaimer, the term of this patent is extended or adjusted under 35 U.S.C. 154(b) by 609 days.

(21) Appl. No.: 14/802,422

(22) Filed: Jul. 17, 2015

(65) Prior Publication Data

US 2016/0015381 A1    Jan. 21, 2016

Related U.S. Application Data

(63) Continuation of application No. 13/584,536, filed on Aug. 13, 2012, now Pat. No. 9,125,644.
(Continued)

(51) Int. Cl.
*A61B 17/04* (2006.01)
*A61B 17/062* (2006.01)
*A61B 90/00* (2016.01)

(52) U.S. Cl.
CPC ...... *A61B 17/0469* (2013.01); *A61B 17/0467* (2013.01); *A61B 17/0493* (2013.01);
(Continued)

(58) Field of Classification Search
CPC .............. A61B 17/0469; A61B 17/062; A61B 17/0493; A61B 17/0625; A61B 17/0482;
(Continued)

(56) References Cited

U.S. PATENT DOCUMENTS

| 1,676,582 A | 7/1928 | Stuart |
|---|---|---|
| 2,336,690 A | 12/1943 | Karle |

(Continued)

FOREIGN PATENT DOCUMENTS

| GB | 630693 | 10/1949 |
|---|---|---|
| WO | WO 2010/011900 | 1/2010 |

(Continued)

OTHER PUBLICATIONS

U.S. Appl. No. 12/833,006, filed Jul. 9, 2011, McClurg et al.

*Primary Examiner* — Anh T Dang
(74) *Attorney, Agent, or Firm* — Leason Ellis LLP

(57) ABSTRACT

A suturing device of the present invention is in the form a compact, light-weight handheld device that includes a needle and suture assembly, a mechanism for gripping and releasing the needle/suture (a "needle transfer mechanism" or "needle shuttle mechanism"), safely capturing the needle/suture upon exit from the patient's tissue, and returning the needle to a position such that the process of delivering additional sutures to the patient can be repeated. A safety shield mechanism ensures the user is protected from the needle at all times. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique.

21 Claims, 17 Drawing Sheets

Related U.S. Application Data

(60) Provisional application No. 61/523,356, filed on Aug. 14, 2011, provisional application No. 61/595,310, filed on Feb. 6, 2012, provisional application No. 61/602,052, filed on Feb. 22, 2012.

(52) U.S. Cl.
CPC .... *A61B 17/062* (2013.01); *A61B 2017/0498* (2013.01); *A61B 2090/0811* (2016.02)

(58) Field of Classification Search
CPC ............ A61B 17/0485; A61B 17/0491; A61B 2017/0498
See application file for complete search history.

(56) References Cited

U.S. PATENT DOCUMENTS

| | | | |
|---|---|---|---|
| 4,109,428 A | 8/1978 | Aarons | |
| 4,373,530 A | 2/1983 | Kilejian | |
| 4,406,237 A | 9/1983 | Eguchi et al. | |
| 4,414,908 A | 11/1983 | Egochi et al. | |
| 4,608,800 A | 9/1986 | Fredette | |
| 4,621,640 A | 11/1986 | Mulhollan et al. | |
| 4,935,027 A | 6/1990 | Yoon | |
| 4,957,498 A | 9/1990 | Caspari et al. | |
| 4,969,302 A | 11/1990 | Coggan et al. | |
| 5,234,443 A | 8/1993 | Phan et al. | |
| 5,426,901 A | 6/1995 | Indracek | |
| 5,437,681 A | 8/1995 | Meade et al. | |
| 5,454,823 A | 10/1995 | Richardson et al. | |
| 5,457,923 A | 10/1995 | Logan et al. | |
| 5,499,990 A | 3/1996 | Schulken et al. | |
| 5,571,090 A | 11/1996 | Sherts | |
| 5,571,119 A | 11/1996 | Atala | |
| 5,609,597 A | 3/1997 | Lehrer | |
| 5,643,292 A | 7/1997 | Hart | |
| 5,665,109 A | 9/1997 | Yoon | |
| 5,694,726 A | 12/1997 | Wu | |
| 5,709,693 A | 1/1998 | Taylor | |
| 5,728,113 A | 3/1998 | Sherts | |
| 5,729,933 A | 3/1998 | Strength | |
| 5,730,747 A | 3/1998 | Ek et al. | |
| 5,746,751 A | 5/1998 | Sherts | |
| 5,759,188 A | 6/1998 | Yoon | |
| 5,766,186 A | 6/1998 | Faraz et al. | |
| 5,824,009 A | 10/1998 | Fokuda et al. | |
| 5,843,100 A | 12/1998 | Meade | |
| 5,860,992 A | 1/1999 | Daniel et al. | |
| 5,871,488 A | 2/1999 | Tovey et al. | |
| 5,897,563 A | 4/1999 | Yoon et al. | |
| 5,904,692 A | 5/1999 | Steckel et al. | |
| 5,908,428 A | 6/1999 | Scirica et al. | |
| 5,919,202 A | 7/1999 | Yoon | |
| 5,935,149 A | 8/1999 | Ek | |
| 5,951,575 A | 9/1999 | Boldue et al. | |
| 5,954,733 A | 9/1999 | Yoon | |
| 5,957,937 A | 9/1999 | Yoon | |
| 5,984,932 A | 11/1999 | Yoon | |
| 5,993,466 A | 11/1999 | Yoon | |
| 5,993,467 A | 11/1999 | Yoon | |
| 6,026,616 A | 2/2000 | Gibson | |
| 6,048,351 A | 4/2000 | Gordon et al. | |
| 6,071,289 A | 6/2000 | Stefanchik et al. | |
| 6,099,550 A | 8/2000 | Yoon | |
| 6,099,553 A | 8/2000 | Hart et al. | |
| 6,159,224 A | 12/2000 | Yoon | |
| 6,224,614 B1 | 5/2001 | Yoon | |
| 6,277,132 B1 | 8/2001 | Brhel | |
| 6,533,795 B1 | 3/2003 | Tran et al. | |
| 6,539,675 B1 | 4/2003 | Gile | |
| 6,643,990 B2 | 11/2003 | Jensen | |
| 6,911,034 B2 | 6/2005 | Nobles et al. | |
| 6,923,819 B2 | 8/2005 | Meade et al. | |
| 6,984,237 B2 | 1/2006 | Hatch et al. | |
| 6,997,932 B2 | 2/2006 | Dreyfuss et al. | |
| 7,011,668 B2 | 3/2006 | Sancoff et al. | |
| 7,033,370 B2 | 4/2006 | Gordon et al. | |
| 7,060,077 B2 | 6/2006 | Gordon et al. | |
| 7,090,686 B2 | 8/2006 | Nobles et al. | |
| 7,108,700 B2 | 9/2006 | Chan et al. | |
| 7,188,454 B2 | 3/2007 | Mowery et al. | |
| 7,316,694 B2 | 1/2008 | Reinitz | |
| 7,318,282 B2 | 1/2008 | Pulte | |
| 7,326,221 B2 | 2/2008 | Sakamoto et al. | |
| 7,331,970 B2 | 2/2008 | Almodovar et al. | |
| 7,338,504 B2 | 3/2008 | Gibbens et al. | |
| 7,442,198 B2 | 10/2008 | Gellman et al. | |
| 7,544,199 B2 | 6/2009 | Bain et al. | |
| 7,572,265 B2 | 8/2009 | Stone et al. | |
| 7,582,096 B2 | 9/2009 | Gellman et al. | |
| 7,588,583 B2 | 9/2009 | Hamilton et al. | |
| 7,615,059 B2 | 11/2009 | Watschke et al. | |
| 7,628,796 B2 | 12/2009 | Shelton et al. | |
| 7,704,262 B2 | 4/2010 | Bellafiore et al. | |
| 7,746,179 B1 | 7/2010 | Schiedegger et al. | |
| 7,748,179 B2 | 7/2010 | Schiedegger et al. | |
| 7,793,475 B2 | 9/2010 | Riggs | |
| 7,997,043 B1 | 8/2011 | MacMillan et al. | |
| 7,998,149 B2 | 8/2011 | Hamilton et al. | |
| 8,006,441 B2 | 8/2011 | Pulte | |
| 8,172,860 B2 | 5/2012 | Zung et al. | |
| 8,252,007 B2 | 8/2012 | Hamilton et al. | |
| 8,257,371 B2 | 9/2012 | Hamilton et al. | |
| 8,282,657 B2 | 10/2012 | McClurg et al. | |
| 8,317,805 B2 | 11/2012 | Hamilton et al. | |
| 8,419,754 B2 | 4/2013 | Laby et al. | |
| 8,603,113 B2 | 12/2013 | Hamilton et al. | |
| 8,617,187 B2 | 12/2013 | Hamilton et al. | |
| 8,685,045 B2 | 4/2014 | Hamilton et al. | |
| 8,758,391 B2 | 6/2014 | Swayze | |
| 2002/0087178 A1 | 7/2002 | Nobles et al. | |
| 2002/0088189 A1 | 7/2002 | Honda | |
| 2002/0124485 A1 | 9/2002 | Pulte | |
| 2003/0023250 A1 | 1/2003 | Watschke | |
| 2003/0181926 A1 | 9/2003 | Dana | |
| 2004/0092967 A1* | 5/2004 | Sancoff ............ A61B 17/0469 606/148 |
| 2004/0243147 A1 | 12/2004 | Lipow | |
| 2005/0043747 A1 | 2/2005 | Field et al. | |
| 2005/0085857 A1 | 4/2005 | Peterson et al. | |
| 2005/0119670 A1 | 6/2005 | Kerr | |
| 2005/0234479 A1 | 10/2005 | Hatch et al. | |
| 2005/0267529 A1 | 12/2005 | Crockett et al. | |
| 2006/0069396 A1 | 3/2006 | Meade et al. | |
| 2006/0075712 A1 | 4/2006 | Gilbert et al. | |
| 2006/0196144 A1 | 9/2006 | Spek | |
| 2006/0282088 A1 | 12/2006 | Ryan | |
| 2007/0021755 A1 | 1/2007 | Almodovar | |
| 2007/0060930 A1 | 3/2007 | Hamilton et al. | |
| 2007/0060931 A1 | 3/2007 | Hamilton et al. | |
| 2007/0062140 A1 | 3/2007 | Sillik | |
| 2007/0088372 A1 | 4/2007 | Gellman et al. | |
| 2007/0225735 A1 | 9/2007 | Stone et al. | |
| 2007/0270885 A1 | 11/2007 | Weinert et al. | |
| 2008/0243147 A1 | 10/2008 | Hamilton et al. | |
| 2008/0249545 A1 | 10/2008 | Shikhman | |
| 2009/0012538 A1 | 1/2009 | Saliman et al. | |
| 2009/0024145 A1 | 1/2009 | Meade et al. | |
| 2009/0157105 A1 | 6/2009 | Zung et al. | |
| 2009/0292300 A1 | 11/2009 | Hamilton et al. | |
| 2010/0010512 A1 | 1/2010 | Taylor et al. | |
| 2010/0016868 A1 | 1/2010 | Kim | |
| 2010/0030238 A1 | 2/2010 | Viola et al. | |
| 2010/0063519 A1 | 3/2010 | Park | |
| 2010/0152751 A1 | 6/2010 | Meade et al. | |
| 2010/0268257 A1 | 10/2010 | Hamilton et al. | |
| 2010/0280530 A1 | 11/2010 | Hashiba | |
| 2011/0251627 A1 | 10/2011 | Hamilton et al. | |
| 2011/0313433 A1 | 12/2011 | Woodard, Jr. et al. | |
| 2012/0165837 A1 | 6/2012 | Belman et al. | |
| 2012/0185637 A1 | 6/2012 | Belman et al. | |
| 2012/0316580 A1 | 12/2012 | Belman et al. | |
| 2013/0041388 A1 | 2/2013 | Lane et al. | |

(56) References Cited

U.S. PATENT DOCUMENTS

| | | |
|---|---|---|
| 2013/0165954 A1 | 6/2013 | Dreyfuss et al. |
| 2013/0231687 A1 | 9/2013 | Laby et al. |
| 2013/0245646 A1 | 9/2013 | Lane et al. |
| 2013/0267969 A1 | 10/2013 | Martin et al. |
| 2013/0304096 A1 | 11/2013 | Nguyen et al. |
| 2014/0222036 A1 | 8/2014 | Hamilton et al. |
| 2014/0276988 A1 | 9/2014 | Tagge et al. |
| 2014/0276989 A1 | 9/2014 | Lane et al. |
| 2014/0288581 A1 | 9/2014 | Hamilton et al. |
| 2015/0335326 A1 | 11/2015 | Dolan et al. |

FOREIGN PATENT DOCUMENTS

| | | |
|---|---|---|
| WO | WO 2013/025622 | 2/2013 |
| WO | WO 2013/126748 | 8/2013 |
| WO | WO 2015/179247 | 11/2015 |

\* cited by examiner

APPARATUS AND METHOD FOR SUTURING TISSUE

CROSS REFERENCE TO RELATED APPLICATIONS

The present application is a continuation of U.S. patent application Ser. No. 13/584,536, filed Aug. 13, 2012, which claims the benefit of U.S. patent application Ser. No. 61/523,356, filed Aug. 14, 2011; U.S. patent application Ser. No. 61/595,310, filed Feb. 6, 2012, and U.S. patent application Ser. No. 61/602,052, filed Feb. 22, 2012, each of which is hereby incorporated by reference in its entirety.

TECHNICAL FIELD

The present invention relates to devices and methods for suturing tissue and more specifically, relates to a handheld device that includes a suturing needle, a needle transfer (shuttle) mechanism for selectively gripping and releasing the suturing needle and shuttling the suturing needle between needle grippers to allow capture of the suturing needle upon exit from the patient's tissue and to allow return of the needle to its initial position, thereby allowing the suturing process to start over, and a safety shield mechanism for shielding the suturing needle during the suturing operation including the needle transfer operation.

BACKGROUND

Needles and suture are used throughout the healthcare industry for indications such as wound and incision closure, securing catheters, and affixing implantable meshes, and other medical apparatus. Because needles represent injury and illness risks to the user, there is a need to make needle usage safer without sacrificing ease of use, performance, and cost. A medical device that can be used to safely suture the tissue of a patient is valuable and appealing to physicians, surgeons, nurses, physician assistants, military personnel, and other clinical and non-clinical users of suture. As described herein, the present invention overcomes the disadvantages of conventional suturing devices and provides a device that has a number of mechanisms that not only shield the needle during operation but also provide a needle shuttling action to ensure effective and complete suturing.

SUMMARY

A device according to one exemplary embodiment is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation (pivoting) suture delivery technique that is familiar to a user based on experience with other surgical techniques.

In one embodiment, a device for suturing tissue includes a handle including a housing having a distal end and an opposite proximal end and a suturing needle having a first pointed end and an opposite second end. The device further includes a first needle gripper coupled to the housing. The first needle gripping element being movable between a first position in which the suturing needle can freely move relative thereto and a second position in which in the suturing needle is held by the first needle gripping element.

A second needle gripping element is coupled to the housing. The second needle gripping element is movable between a first position in which the suturing needle can freely move relative thereto and a second position in which in the suturing needle is held by the second needle gripping element.

The device includes an actuator disposed within the housing and operatively coupled to the second needle gripping element for moving the second needle gripping element between the first and second positions. A safety mechanism is coupled to the housing and configured for shielding the pointed end of the needle, wherein prior to insertion of the suturing needle into the tissue, the suturing needle is held by the first needle gripping element and subsequent to passage of the suturing needle through the tissue and upon activation of the actuator, the suturing needle is released from the first gripping element and is captured and held by the second needle gripping element to allow retraction of the suturing needle from the tissue.

A device for suturing tissue according to one embodiment includes a handle having a distal end and an opposite proximal end and being rotatable (pivotable) about a first axis and a suturing needle having a first pointed end and an opposite second end. The device further includes a needle gripping mechanism disposed within the handle and including first and second needle grippers. The first needle gripper is movable between a first position in which the suturing needle can freely move relative thereto and a second position in which in the suturing needle is securely held thereby.

A second needle gripper is coupled to the handle. The second needle gripper is movable between a first position in which the suturing needle can freely move relative to the second needle gripper and a second position in which in the suturing needle is held by the second needle gripper. The device also includes an actuator disposed within the handle and operatively coupled to the needle gripping mechanism for shuttling the suturing needle between the first and second grippers. In a first operating position prior to insertion of the suturing needle into the tissue, the handle is positioned at a first acute angle relative to a tissue surface and the device is configured such that movement of the handle about the first axis from the first position to a second operating position in which the handle is positioned at a second acute angle relative the tissue surface causes the suturing needle to be driven into and through the tissue and permits capture of the first pointed end by the second gripping element upon activation of the actuator.

A device for suturing tissue according to one embodiment includes a handle having a distal end and an opposite proximal end and being rotatable about a first axis and a suturing needle having a first pointed end and an opposite second end. The device also includes a needle gripping mechanism disposed within the handle and including first and second needle grippers. The first needle gripper is movable between a first position in which the suturing needle can freely move relative thereto and a second position in which in the suturing needle is securely held thereby.

A second needle gripper is coupled to the handle. The second needle gripper is movable between a first position in which the suturing needle can freely move relative to the second needle gripper and a second position in which in the suturing needle is held by the second needle gripper. In addition, an actuator is disposed within the handle and operatively coupled to the needle gripping mechanism for shuttling the suturing needle between the first and second grippers.

In a first operating position prior to insertion of the suturing needle into the tissue, the handle is positioned at a first acute angle relative to a tissue surface and the device is configured such that movement of the handle about the first axis from the first position to a second operating position in which the handle is positioned at a second acute angle relative the tissue surface causes the suturing needle to be driven into and through the tissue and permits capture of the first pointed end by the second gripping element upon activation of the actuator.

According to one exemplary embodiment, a device for suturing tissue includes a handle having a distal end and an opposite proximal end and being rotatable (pivotable) about a first axis. The device also includes a suturing needle having a first pointed end and an opposite second end. A needle shuttle mechanism is coupled to the handle and includes a first part and a second part. Each of the first and second parts is movable between a needle release position in which the suturing needle can freely move relative thereto and a needle retaining position in which the suturing needle is captured and held thereby. The second part is rotatable (pivotable) about the first axis.

An actuator is disposed within the handle and is operatively coupled to the needle shuttle mechanism for causing the suturing needle to be shuttled between the first and second parts to permit the suturing needle to be driven into and passed through the tissue. The device also includes a safety mechanism coupled to the housing and configured for shielding the pointed end of the needle. The safety mechanism is rotatable about the first axis independent from the rotation of the needle shuttle mechanism about the same first axis.

According to one exemplary embodiment, a device for suturing tissue includes a handle having a distal end and an opposite proximal end and being rotatable (pivotable) about an axle that extends along a first axis, in response to rotational movement of a user's hand. The device also includes a suturing needle having a first pointed end and an opposite second end. A needle shuttle mechanism is coupled to the handle and including a first part and a second part. Each of the first and second parts is movable between a needle release position in which the suturing needle can freely move relative thereto and a needle retaining position in which the suturing needle is captured and held thereby. The second part is rotatable (pivotable) about the first axis.

The device also includes an actuator disposed within the handle and operatively coupled to the needle shuttle mechanism for causing the suturing needle to be shuttled between the first and second parts. Wherein prior to insertion of the suturing needle into the tissue, the handle is positioned at a first acute angle relative to a tissue surface and the device is configured such that rotation of the handle about the first axis to a different position, in which the handle is positioned at a second acute angle relative the tissue surface, causes the suturing needle to be manually driven into and through the tissue and permits capture of the first pointed end by the second part upon activation of the actuator.

The present invention is also directed to a method for suturing tissue using one device described herein. The suturing action is performed in part by rotating (pivoting) the handle about and axis of the device from one position to another position and in particular, the first and second positions can be positions at which the handle is at an acute angle relative to the tissue.

BRIEF DESCRIPTION OF DRAWING FIGURES

DETAILED DESCRIPTION OF CERTAIN EMBODIMENTS

Figure 2:
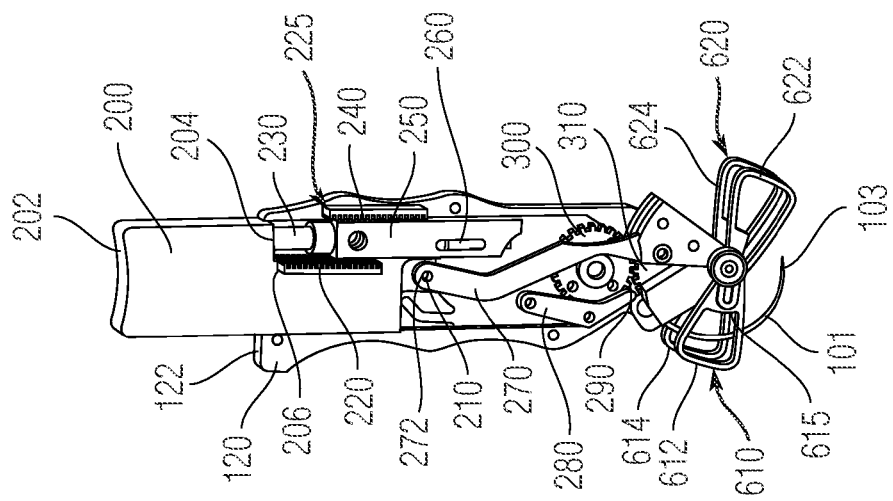
FIG. 2 is a side perspective view showing internal components of the device of FIG. 1.

The present invention is directed to devices and methods for safely suturing tissue, skin, muscle, ligament, tendon and similar structures. Healthcare workers need a safe device and method for closing wounds and incisions and for securing catheters to a patient. The current procedure typically consists of a user grasping an unprotected needle and suture with hemostats, a needle driver, or forceps and then piercing the patient's tissue by utilizing hand and wrist movements. In this scenario, the needle point is exposed to the user throughout the procedure and provides risk for accidental needle stick injuries (NSI) to the user and procedural staff. These NSIs can transmit blood borne pathogens such as hepatitis and HIV to the user and others from the patient and potentially cause illness or death. Users that are injured in this manner are required to report the injury, undergo diagnostic tests and begin receiving prophylactic treatment. They may also be required to take a leave of absence from work or continue indefinitely with a prescribed drug regimen.

As described in great detail below, a device according to the present invention is a compact, light-weight handheld device that includes a needle and suture assembly, a mechanism for gripping and releasing the needle and suture assembly (a "needle transfer mechanism" or "needle shuttle mechanism"), safely capturing the needle assembly upon exit from the patient's tissue, and returning the needle to a position such that the process of delivering additional sutures to the patient can be repeated. The device of the present invention accommodates the right or left-handed user, rests comfortably in the user's hand, allows sufficient visualization of the procedure site, and permits the user to either control penetration depth of the needle or default to a device-determined depth. The present device permits the user to utilize a wrist-rotation suture delivery technique that is currently employed for securing a catheter, closing a wound, or in related procedures.

The suturing device of the present invention offers a number of advantages compared to other conventional suturing devices. The following are merely some of the advantages provided by the present device: (1) safety: the user cannot contact the point of the needle and is able to avoid accidental NSIs and the human and financial costs associated with those accidents; (2) performance: the device allows the user to reproduce the needle motion that is currently used by healthcare workers. This improves the accuracy and integrity of the securement and reduces the trauma to the patient; (3) size: the device is sized and oriented for easy access to crowded and narrow regions of the patient's body such as the neck; (4) ease of use: the device can be generally operated with one hand and multiple sutures are able to be secured to the patient through a minimal series of steps; (5) cost: the device is designed as a single use device that is economical and easy to manufacture; (6) versatility: the device is suitable for use within a hospital environment and any first aid setting. It can be utilized to secure nearly every type of catheter and to close wounds. In addition, it may be packaged within catheter and medical accessory sets or as a stand-alone device.

In one exemplary embodiment, the suturing needle within the present device can be returned to its starting point after it crosses the patient's tissue so that the device can be used to repeat the needle delivery process. At the conclusion of the process, the suturing needle is safely retained by the needle transfer mechanism within the device, which can then be safely disposed. In one exemplary embodiment, safety features (include the safety shield mechanism) are incorporated into the suturing device such that the user cannot come into contact with the suturing needle before, during, and after the procedure. In addition, an integral cutter is preferably incorporated into the suturing device in order that the suture can be cut by the user without the need for scissors or a scalpel.

Although in one embodiment, the present device is intended to be a single-use device, it is understood that slight alterations can be made to the design and materials that would allow said device to be resterilized, reloaded with an additional needle and suture assembly, and reused.

The suturing device includes a handle, which as described in detail below, is comprised of one or more components and can be molded, cast or extruded from a variety of materials including but not limited to polymers or metals. Examples of polymers suitable for fabricating the handle are thermoplastics and thermosetting materials such as polystyrene, acrylic, polycarbonate, polyamide, polyester, polyetherimide, polysulfone, polylactic acid, polyvinylchloride, polyolefins, polyurethane, fluoropolymers, and copolymers and alloys thereof. These materials may be filled with glass or other useful reinforcing agents in order to enhance their mechanical properties. Suitable metals come from but are not limited to a group including titanium alloys and stainless steel. The selected materials must meet physical and mechanical performance requirements and be able to withstand sterilization methods employed within the medical device industry such as ethylene oxide or gamma irradiation.

According to one exemplary embodiment, the needle assembly generally consists of a suturing needle and a suture attached thereto. The suturing needle includes a distal pointed end suitable for piercing and crossing tissue and a blunt proximal end suitable for affixing a suture, and a body between the distal and proximal ends. The suturing needle can be fabricated in a variety of configurations from straight to curved and be monolithic or of a multi-part construction. The outer diameters of the needles can be round or nonround, tapered, or possesses features that assist in advancing and gripping the needle. Needles are commonly made from stainless steel and related alloys but can be made from other metals, polymers and ceramic materials that are sufficiently rigid, capable of possessing and sustaining a functionally sharp distal point, and able to bond to suture. Traditionally, sutures are affixed to the proximal end of metal needles by swaging, crimping, and adhesives. Suture attachment can also be configured such that the suture is affixed to the other regions of the needle, yet not the proximal terminus. This design variant provides additional freedom for suture management and gripping the needle in the device handle. Coatings on the needle serve to enhance the lubricity of the needle and reduce tissue penetration forces.

The suture is the thread-like structure that is used to close wounds and incisions or to secure catheters or other components to patients. The suture can come in a variety of diameters, textures, forms, i.e., single strand or braided, and materials depending upon the desired properties and intended application. Sutures can be absorbable, i.e., collagen, polyglactin, polydioxanone, polyglycolide-lactide copolymers, or non-absorbable, i.e., silk, nylon, polyester, polypropylene. Sutures can be treated with antimicrobial, bioabsorbable, hydrophilic or other functional additives. In addition, sutures can be textured with raised "unidirectional" features, which permit the suture to pass easily through tissue when drawn in one direction, however, impedes the suture from being pulled out of the tissue when it is drawn in the reverse direction.

The interfaces between the handle and the suturing needle/suture are generally referred to as the mechanisms or assemblies. These mechanisms serve to grasp, release, and shuttle the needle by manipulations to the handle by the user or by otherwise manipulating the device to cause the needle transfer. As will be appreciated from the below detailed description, there are a number of mechanical mechanisms that can be used to produce the desired movement of the suturing needle and more specifically, produce a reciprocal needle transfer action in which the suturing needle is initially held in one position within the mechanism and is then caused to be moved to another position within the mechanism to effectuate the suture needle passing into and through the tissue and then being subsequently extracted from the tissue. Further, after extraction, the mechanism is preferably designed to pass the suturing needle back from the needle capture/extraction position to the initial position at which the process can be repeated. Thus, one mechanism can be thought of as being a mechanism for cycling the suturing needle between different positions that result in the desired suturing action.

It will thus be appreciated that a variety of mechanisms that are able to grasp, release, and shuttle the needle can be used. The mechanisms include but are not limited to rack and pinion, gearing, cams, ramps, screw bodies, springs, multiple-point gripping structures, i.e., 3-point, collets, drive belts, and rigid and flexible push rods to name a few. In instances, the suturing needle can comprise physical features that correspond to engagement features found within these mechanisms in order, for example, to increase grip strength. Some examples of these features are indentations, serrations, projections, faces, flats, undercuts, rings, and ports.

Moreover, the present device preferably includes a safety shield mechanism, which protects the user from the needle point before, during, and after the suturing procedure. The safety shield mechanism can exist in numerous forms in that any number of different mechanical arrangements can be used to accomplish the intended function. The safety shield mechanism can comprise single or multiple components, be biased to a safety-mode position and/or be user actuated, and/or have reversible or irreversible lock-out features as described further herein. The safety shield mechanism can be configured, for example, as a slideable or rotatable cover, or as deflectable wing-like shields that obstruct user access to the needle point. Similar to the handle described above, the safety shield mechanism cans be made from a wide range of thermoplastics and thermosetting polymers; however, a transparent polymer may be more desired as it would provide the user with greater visibility of the needle and suturing site. Furthermore, the safety shield mechanism can be manufactured from metals, such as stainless steel, titanium, and titanium alloys including nickel-titanium, and configured as a wire-form, mesh, grid, or strut. A spring or other force-resilient components can be incorporated in order to bias the safety apparatus into a safe position or to actuate multiple components that comprise the safety apparatus.

Finally, a suture cutter is preferably located within the device handle so that the user can trim knotted sutures and suture strands to length. One exemplary cutter can be a dynamic shearing apparatus, i.e., scissors or slideable blade(s), that requires the user to press or slide a button or manipulate an actuator having a different form, such as a knob or lever, in order to actuate the blade to cut the suture. To this end, the suture(s) can be positioned in a notch, slot, or hole located on the handle, and the actuation of the sharpened blade would cut the suture(s). Upon cutting the suture, a spring or similar component would return the blade to its original position such that the cutting process can be repeated. Alternatively, the cutter can be a simple apparatus such as a static cutting blade located in a narrowing, crevice-like feature on the handle. In this configuration, the suture could be drawn across the sharp edge of the blade in order to cut it. Typical materials that are useful as cutting blades are stainless steel, carbon steel, and gemstones, such as diamond. For safety purposes, the user does not have direct access to the cutting blade; only suture is able to reach the blade via the suture cutter notch or hole. Beyond the safety advantage, the integral cutter would reduce or eliminate the need for the user to provide a separate pair of scissors for cutting or trimming suture during the procedure.

It will be appreciated that the above-described structures constitute exemplary parts of one suturing device according to the present invention and each of these structures is described in greater detail below. The foregoing discussion is thus a brief summary of suitable parts that can be present within the present suturing device; however, are not to be considered to be limiting of the scope of the present invention. The make-up and operation of various exemplary suturing devices in accordance with the present invention are now described.

FIGS. 1-6 illustrate a suturing device 100 according to one exemplary embodiment. The suturing device 100 is formed of a number of components/parts, assemblies and mechanisms that operate to perform the intended suturing action as described herein.

The suturing device 100 includes a housing that contains a number of the working components and allows a user to easily hold and use the device 100. For example and as shown in the illustrated embodiment, the housing can be in the form of an elongated handle that is formed of a first part 110 and a second part 120. The first and second parts 110, 120 are complementary to one another and include a means for attaching the two parts together to form an assembled handle that can be easily grasped and manipulated by the user. For example, the first and second parts 110, 120 can be attached to one another by a mechanical attachment, such as by using fasteners, by establishing a snap-fit between the two parts, etc. The handle not only houses many of the working components but also provides a means for the user to grasp the device 100 but also manipulate it in such a way to cause the needle 101 to be advanced into and through the tissue 10 and then exists the tissue 10.

Each of the first and second parts 110, 120 is generally hollow and therefore, when the two handle parts 110, 120 are attached to one another, they define a hollow interior handle space that receives and holds many of the working components of the device 100 as will be appreciated below. The first part 110 is an elongated handle part defined by a proximal end (upper end) 112 and a distal end (bottom end) 114 and similarly, the second part 120 is an elongated handle part that is defined by a proximal end (upper end) 122 and a distal end (bottom end) 124. The handle can include ergonomic gripping regions/surfaces 109 suitable for both left and right-handed users to facilitate grasping of the device 100. As shown, these gripping regions 109 can be in the form of locally recessed and contoured portions of the handle that locate and permit a user's thumb/fingers to grasp the exterior of the device 100. The gripping regions 109 can alternatively be defined by a modified exterior surface of the housing parts 110, 120 within local handle sections that allow the user to more easily grasp the handle. For example, the exterior surface of the handle can be a rough surface defined by surface features, such as a plurality of raised bumps or the like or can even be defined by a material that is different than the material of the handle and is applied thereto (e.g., a gripping surface member applied to the handle by means of an adhesive or over-molding process or other suitable process).

As shown in the figures and described in detail herein, the suturing device 100 is configured to move a curved suturing needle 101 in a controlled manner such that the suturing needle is advanced into and through target tissue 10 and is then extracted from the tissue 10 to complete one suturing action and allow the user to tie off the suture element itself. As mentioned herein, any number of different types of suturing needles 101 can be used with the device 100. In general, the suturing needle 101 includes a sharp distal end 103 for penetrating the tissue 10 and an opposite proximal end 105 (see, FIG. 4) which is typically a blunt end.

The device 100 also includes an actuator assembly that is used to operate the device 100 and to effectuate the controlled movement (shuttle action) of the suturing needle 101. The actuator assembly includes an actuator body 200 that is accessible to the user and is manipulated by the user to cause controlled movement of the suturing needle 101. In the illustrated embodiment, an upper end 202 of the actuator body 200 extends beyond the proximal end of the handle and is accessible by the user. The actuator body 200 is operatively coupled to other parts of the actuator assembly to cause the desired controlled movement as described hereinbelow and in particular, causes needle transfer to effectuate the suturing action.

It will be appreciated that the illustrated actuator assembly is merely one exemplary type of actuator that can be used in the present device 100 to cause controlled movement of the suturing needle 101 and there are a number of other actuator assemblies that can be used for causing the needle to be transferred (shuttled) in the manner described herein. For example, while the actuator body 200 is moved linearly by the user (e.g., as by pressing down on the end 202 of the body 200), other actuators suitable for use in the present invention can be activated by other techniques, such as pressing a button, rotating an actuator element, etc.

In the illustrated embodiment, the actuator body 200 is connected to a needle transfer mechanism 400, which as mentioned herein, is designed to controllably move the needle 101 from one operating position to another operating position and more specifically, to transfer the suturing needle 101 from one needle transfer structure (member) to another needle transfer structure (member) to allow the suturing needle 101 to be extracted from the tissue 10 once it passes therethrough. The connection can be achieved by using a linkage, such as by using a link arm 270 that is coupled to the actuator body 200 at one end thereof. In particular, the handle part 120 can include a feature, such as a protrusion (boss) 210, that is received within an opening 272 formed in one end of the link arm 270, thereby defining a pivot between the link arm 270 and the body 200. Movement of the actuator body 200 is translated into movement of the link arm 270 to thereby drive the needle transfer mechanism 600 and in the illustrated embodiment, the link arm 270 is depressed and causes the link arm 270 to move downward. The link arm 270 includes an opening 274 at a distal end that is configured for coupling the link arm 270 to the needle transfer mechanism 600.

In accordance with one embodiment, the actuator assembly includes a drive mechanism 225 for generating a return force that is applied to the actuator body 200 to automatically return the actuator body 200 to a rest position upon release of the actuator body 200. As a result, the drive mechanism 225 can be thought of as at least partially being a return mechanism that returns the actuator body 200 to its original position when the actuator force applied to the actuator body 200 is removed. It will be understood and appreciated that the illustrated drive mechanism 225 is merely one type of mechanism for returning the actuator body 200 to the rest position and there are many other mechanical arrangements that can accomplish the same movement and same function as the mechanism 225. The drive mechanism 225 includes a first rack 220 that is carried by the actuator body 200 and therefore, moves in unison therewith, and a second rack 240 that is fixedly coupled to the handle part 120. Each of the first and second racks 220, 240 includes a series of teeth.

Figure 1:
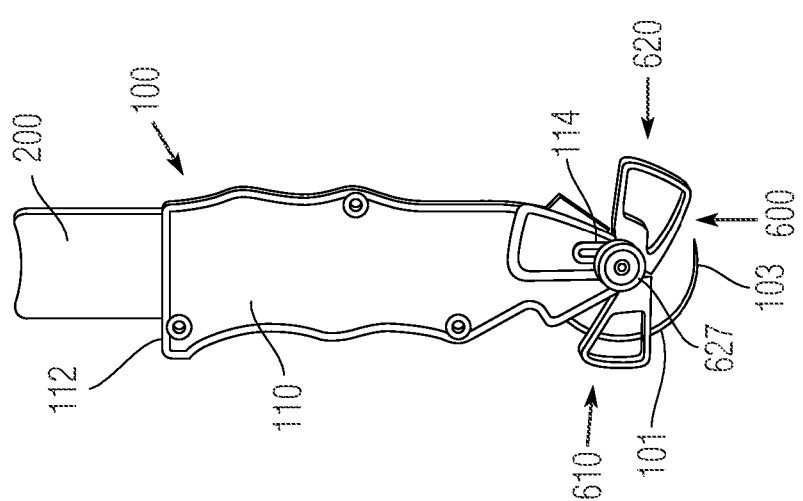
FIG. 1 is a side elevation view of a suturing device according to one exemplary embodiment.
Figure 4:
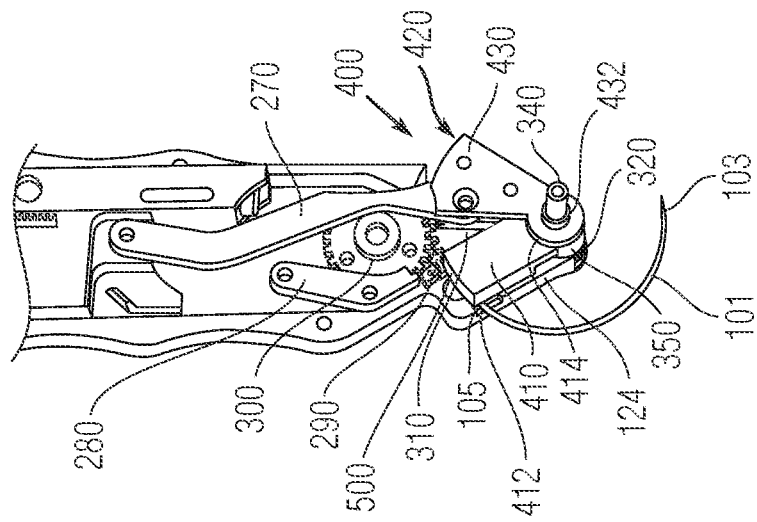
FIG. 4 is a side perspective showing, in close-up, a needle transfer (shuttle) mechanism according to one exemplary embodiment and located at a distal end of the device.
Figure 3:
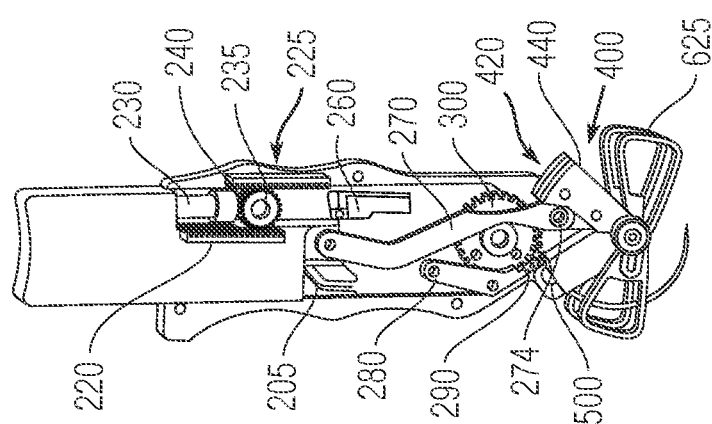
FIG. 3 is a side perspective view showing internal components of the device of FIG. 1.
Figure 5:
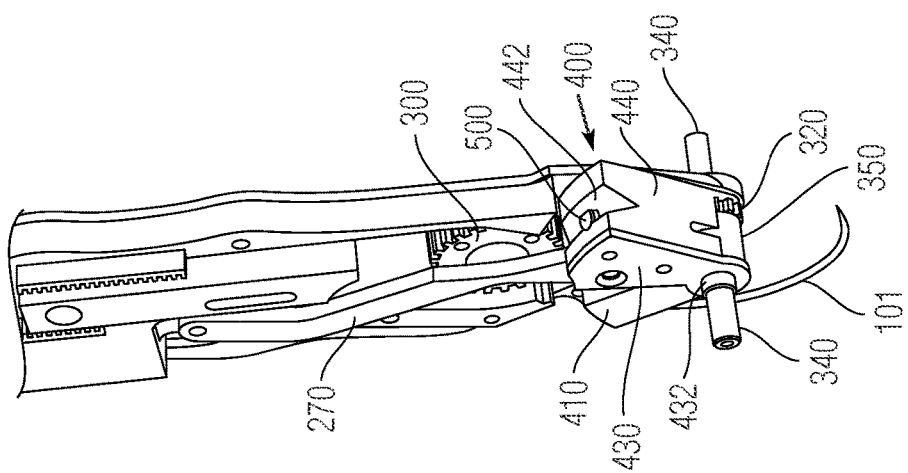
FIG. 5 is a side and end perspective view of the distal end of the device including the needle transfer mechanism.

The illustrated drive mechanism 225 is based on applying a biasing force to the actuator body 200 to cause the actuator body 200 to normally (in a rest position) assume an upward position (see FIGS. 1-2). The biasing force is generated by a biasing member, such as a spring (not shown) that exerts a biasing force that is applied to the actuator body 200 to drive the actuator body 200 upward.

The biasing force can be generated by a spring that is disposed within a spring housing 250 that contains the spring and also includes a rotatable gear 235 that meshes within the teeth of the racks 220, 240 for controlled linear movement of the actuator body 200 as the body 200 is depressed by the user and when a return force is automatically generated to return the actuator body 200. A return spring guide 230 is disposed between the housing 250 and an undercut wall 204 of the actuator body 200. The return spring guide 230 seats flush against the wall 204 and therefore a force applied to the wall 204 results in a driving of the actuator body 200 in an upward direction to return it to its normal rest position. When the user applies a downward force to activate the actuator assembly, this applied force overcomes the biasing force generated by the spring and thus, the actuator body 200 can be driven downward by the user, thereby causing the desired movement of the link arm 270 (in this case, driving the link arm 270 in a downward direction). The illustrated drive mechanism 225 also includes a drive finger 260 is disposed within the housing 250 at a lower end thereof and is configured to move as the actuator body 200 moves in the manner described herein and is configured to allow for rotation of the needle transfer mechanism 400 and permit both capture and return of the suture needle 101 to the original positions.

In accordance with one embodiment, the device 100 includes a number of gears that engage one another to translate movement of the actuator body 200 into movement of the needle transfer mechanism 400. For example, the device 100 can include a first gear 300 that is rotated due to movement of the actuator body 200 and as described below is configured to impart movement to the needle transfer mechanism 400. The first gear 300 is rotatably coupled to the handle housing (i.e., handle part 120) and can include features that are contacted by the drive mechanism 225 for imparting movement of the needle transfer mechanism 400 as described below. For example, the first gear 300 can include upstanding posts (protrusions) (not shown) that are contacted by a part of the drive mechanism (e.g., drive finger 260) or the first gear 300 can otherwise be contacted/engaged by a part of the drive mechanism 225, such as by the drive finger 260 or other structure during the downward movement of the actuator body 200 to cause a rotation of the first gear 300. The drive mechanism 225 is configured such that one actuator cycle movement defined by pressing the body 200 downward to its end of travel causes the drive finger 260 to be driven into engagement with one post associated with the first gear 300 resulting in the first gear 300 making a ¼ rotation. In other words, there can be four posts on the first gear 300 representing four ¼ rotation cycles such that each actuator cycle (unit 200 being pressed down and then released) results in the first gear 300 turning a ¼ rotation. This is merely one exemplary way of obtaining controlled movement of the first gear 300 by means of movement of the actuator assembly.

The device 100 also includes a second gear 310 which meshes with the first gear 300 and is located more distal relative thereto. The second gear 310 is also supported by the handle and in particular is rotatably coupled to one of the handle parts 110, 120.

The second gear 310 is intimately meshed with a third gear 320 which is in the form of a cam gear 320 which is associated with (coupled to) a cam shaft 340 (in one exemplary gear ratio, the gear 300 moves ¼ turn per actuation, while the gear 320 rotates ½ turn). More specifically, the cam shaft 340, which can be thought of as an axle, is located at the distal end of the handle and defines an axis about which not only the handle (parts 110, 120) can rotate but also defines an axis about which other parts of the devices can rotate as described herein. In particular, in one embodiment, the axis defined by the cam shaft 340 defines an axis of rotation of both the needle transfer mechanism 400 and the safety shield mechanism 600. The cam shaft 340 is supported by the handle parts 110, 120 and extends generally perpendicular thereto. By defining an axis of rotation for the handle itself and thus the device 100 itself, the device 100 is designed to rotate about the cam shaft 340 during use of the device 100 in order to initially position the device 100 and then advance the suturing needle 101 into contact with the tissue 10 and then through the tissue 10. This rotation is in contrast to some conventional suturing devices in which the handle is held stationary and the needle is manipulated to cause movement of the needle through the tissue and, as described herein, this construction allows the device 100 to capitalize on traditional rotation of a wrist of the user to cause advancement of the suturing needle 101.

In one aspect and as described herein, the device 100 is thus positioned on target tissue 10 and the suturing action occurs by the user rotating his or her wrist to directly cause the device 100 to move (pivot) relative to the tissue, thereby causing the suture needle 101 to follow an arcuate path into and through the tissue 10. It will be appreciated that one typical pathway of the needle 101 is a compound arc, which has the needle starting out perpendicular and then rotating on a smaller radius in order to create a shallower skin penetration.

The device 100 includes a means for controlling the gear movement and in particular, prevents the gears from reversing their direction. In one embodiment, the means is in the form of a pawl 280 that cooperates with a ratchet member 290 to ensure that the gears do not reverse direction. In the illustrated embodiment, the ratchet 290 engages the first gear 300, while the pawl 280 engages the posts that are associated with and extend from the first gear 300. The pawl 280 and ratchet 290 are supported by the handle housing and move relative thereto to periodically and sequentially engage one gear (in this case, the first gear 300) such that all three gears 300, 310, 320 cannot reverse their direction. This results in the needle transfer mechanism 400 moving and operating in a controlled manner.

The cam shaft 340 includes a cam (cam body) 350 located therealong. The cam 350 is designed in part to cause selective movement of parts of the needle transfer mechanism 600 depending upon the location of the cam 350. The cam action of the shaft 340 is described in detail below and its cooperation with the parts of the needle transfer mechanism 400 serves to allow both secure grasping (holding) of the suturing needle 101 and a clean transfer or shuttle action of the suturing needle 101 from a position prior to advancement into and through the tissue to a position in which the suturing needle 101 is extracted from the tissue 10.

The needle transfer mechanism 400 functions as a needle shuttle mechanism as described above and more specifically, is configured to grasp the suturing needle 101 in one of a number of different operating positions depending upon the position of the device 100 and the suturing stage of the device 100. More specifically, the needle transfer mechanism 400 includes a number of parts that are designed to grasp a first portion of the suturing needle 101 prior to advancement of the suturing needle 101 into the tissue 10 and then subsequently grasp a second portion of the suturing needle 101 after the suturing needle 101 passes through the tissue 10 and is captured by the needle transfer mechanism 400 for extraction of the suturing needle 101 from the tissue 10.

In the illustrated embodiment, the needle transfer mechanism 400 includes a first needle gripper 410 and a second needle gripper 420. The first needle gripper 410 can be in the form of a needle gripping assembly or a needle gripping structure (member) 410 and the second needle gripper 420 can be in the form of a needle gripping assembly or a needle gripping structure (member) 420. It will therefore be understood that a "needle gripper" can be formed of a single part or be in the form of an assembly of several parts that provide a needle gripping structure that selectively grasps and holds the suturing needle 101 and therefore, while one or more of the illustrated needle grippers are formed as an assembly of several parts, it is within the scope of the present invention that the needle gripper can be constructed of a single part that performs the function described herein.

The first needle gripper 410 includes a housing that receives a first reciprocating part 500 that contacts the cam member 350 and is selectively moved as the cam member 350 rotates about the shaft 340. The housing of the first needle gripper 410 includes a first end that has a notch or recess (track) 412 formed therein and includes an end 414 that is disposed proximate the shaft 340. The first needle gripper 410 is coupled to the handle and the notch 412 in combination with a notch formed in the handle part 120 defines a first needle receiving space for selectively receiving the suturing needle 101 when the first reciprocating part 500 is in a needle receiving (open) position.

In the illustrated embodiment, the first needle gripper 410 is a fixed part in that the housing thereof does not move relative to the handle (i.e., it does not rotate relative to the cam shaft 340). However, the first reciprocating part 500 is movable between the needle receiving (open) position in which the suturing needle 101 can freely move relative to the first needle gripper 410 and a needle grasping (closed) position in which the suturing needle 101 is grasped and held by the first needle gripper 410.

Figure 6:
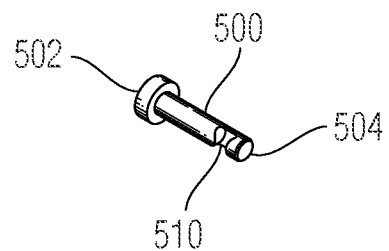
FIG. 6 is a side perspective view of a needle clamping member according to one exemplary embodiment and part of the needle transfer mechanism of FIG. 4.

As shown in FIG. 6, in one embodiment, the first reciprocating part 500 is in the form of a clamp pin that is biased relative to the cam shaft 340 and in particular, relative to the cam member 350 thereof and is received within the first gripper 410. The first reciprocating part 500 is in the form of an elongated pin that includes a first end 502 and an opposite second end 504. The first end 502 can be in the form of an enlarged head and the part 500 includes a shaft portion that is of lesser dimension that the head. For ease of illustration, the part 500 is described and referenced herein as being pin 500; however, other non-pin like structure can be equally used and therefore, the reference as being a pin is not limiting. The shaft includes an opening, notch or slot 510 that is formed therein and is sized and configured to receive the suturing needle 101. When the first reciprocating pin 500 is in the needle receiving position, the notch 510 is in the open (needle receiving) position in which the suturing needle can freely travel within the notch 510. Conversely, in the closed position, the suturing needle 101 disposed within the notch 510 is not free to move relative to the pin 500 but instead, the suturing needle 101 is firmly grasped by the pin 500 by being intimately disposed between the pin 500 and an underlying structure of the first needle gripper 410 (the needle is held within the channel 412).

In accordance with the present invention, the pin 500 is biased relative to the cam shaft 340 (and the cam 350). For example, a biasing element (not shown in FIGS. 1-6) in the form of a spring that is disposed about the pin 500 and causes the pin 500 to be biased relative to the cam shaft 340. In the illustrated embodiment, the pin 500 is biased toward the cam shaft 340; however, it will be appreciated that the pin 500 can be biased in a direction away from the cam shaft in another embodiment. In a rest position, the pin 500 is thus in a closed position in that the pin 500 is biased toward the cam shaft 340 and the needle 101 is held in place since it is received within the notch 510 and the pin 500 is biased inward thereby closing the space between the pin and the first needle gripper 410 that defines the notch 510 intimately contacts and applies a force against the suturing needle 101 so as to grasp the suturing needle 101.

The housing of the first gripper 410 includes an opening that is formed within the notch 412 and allows the shaft of the pin 500 to extend through so as to position at least a portion of the pin 500 within the notch 412 that receives a portion of the suturing needle 101. The pin 500 is positioned within the hollow interior of the first gripper 410 such that the needle receiving notch 510 thereof is in registration with the notch 412, thereby allowing the suturing needle 101 to pass through the notch 412 and through the notch 510 of the pin 500.

The second needle gripper 420 is similar to the first needle gripper 410 in that the second needle gripper 420 is intended to selectively grasp and hold a portion of the suturing needle 101 depending upon the particular stage of the suturing operation. The illustrated second needle gripper 420 includes a needle gripper body or housing 440 that has a first needle receiving end that includes a notch or recess (track) 442 formed therein. The notch 442 is similar or identical to the notch 412 of the first gripper 410 and is designed to freely receive the suturing needle 101 when a second pin 500 is in one of its operating positions (i.e., the needle receiving or open position). In the illustrated embodiment, the notches 412, 442 are V-shaped notches formed in the end that is further from the shaft 340 and cam member 350.

It will be appreciated that the shape of the notch 412 and the shape of the pin 500 are selected in view of one another to provide an effective gripping interface between the two at the location at which the two are in intimate contact. For example, the interface is defined between the V-shaped notch 412 and the needle portion which can have a trapezoidal shape, thereby creating a matched fit between the two structures. It will be appreciated that the shapes of the notch 412 and needle 500 can be different so long as preferably there is the above-described match fit between the two resulting in an effective needle gripping location. The shape of the needle also facilitates the intimate engagement between the pin 500 and the needle 101 since a face (e.g., a flat surface) of the pin 500 can intimately contact a complementary face (e.g., a flat surface) of the suturing needle 101, thereby securely holding the needle in the respective channel.

As with the first needle gripper body 410, the second needle gripper body 440 has an open bottom to allow the second pin 500 contained therein to be in intimate contact with the cam member 350 and the body 440 has an opening formed in the notch 442 that allows passage of the pin 500 therethrough. The second needle gripper body 440 is also configured to be operatively coupled to the link arm 270 to thereby provide a means for transferring the movement of the actuator body 200 into movement of the second needle gripper 420. Thus, unlike the first gripper 410, the second gripper 420 is a movable gripper that can move to different positions and in different directions as described herein. Any number of different means can be used to couple the link arm 470 to the second needle gripper 420 and in the illustrated embodiment, the second needle gripper body 440 includes a protrusion (boss) that is received within the opening 274 that is located at the distal end of the link arm 270. This arrangement allows the second gripper 420 to rotate relative to the cam shaft 340 upon activation of the actuator and in particular in response to movement of the actuator body 200. As a result of the above arrangement and mechanical coupling of parts, the downward and upward movement of the actuator body 200 causes a pivoting of the second needle gripper 420 about the cam shaft 340. As described herein and appreciated by viewing the figures, downward movement of the actuator body 200 is translated into pivoting of the second needle gripper 420 in a direction away from the handle and toward the distal end of the device 100. Conversely, when actuator body 200 is moved in an upward direction, the second needle gripper 420 pivots about cam shaft 340 in the opposite direction (i.e., in a direction back towards the handle).

As mentioned above, the pins 500 are biased and in the illustrated embodiment, are biased towards the cam shaft 340. However, in another embodiment, the pins 500 are biased in the opposite direction (i.e., in a direction away from the cam shaft 340). In both embodiments, the pins 500 are moved as the cam member 350 makes contact with the pins 500 as the cam member 350 rotates about the shaft 340. Contact with the cam member 350 thus urges the respective pin 500 in a desired direction. In either embodiment, the suturing needle 101 is freely to move relative to the pin 500 and thus be both initially received and subsequently free to be released from the pin 500 when the pin 500 is in the open position and conversely, when the pin 500 assumes the closed position, the suturing needle 101 is grasped by the respective needle gripper.

The second needle gripper 420 also can include a side plate 430 that is coupled to the needle gripper body 440 so as to cover the coupling between the link arm 270 and the needle gripper body 440 and also provides a means for coupling the second needle gripper 420 to the cam shaft 430. More specifically, the side plate 430 has a distal end portion that includes an opening 432 that receives the cam shaft 340. As shown, the opening 432 can be surrounded by an annular shaped wall or flange that contacts yet is rotatable about the cam shaft 340. The side plate 430 is located adjacent the cam member 350, while the first needle gripper body and the second needle gripper body are adjacent the cam member 350 since the pins 500 contained therein are in contact with the cam member 350.

The safety shield mechanism 600 is configured to shield the suturing needle 101 during the operation of the device 100 and the controlled movement of the suturing needle 101, thereby protecting the user from undesired contact with the suturing needle 101. In the illustrated embodiment, the safety shield mechanism 600 is formed of a pair of safety shields 610, 620 that are freely movable relative to the handle and are positioned and constructed such that as the suturing needle 101 is advanced into the tissue 10 and then subsequently exits the tissue 10 and is captured by the needle transfer mechanism 400, the safety shields 610, 620 shield the sharp end 103 of the suturing needle 101. Each safety shield 610, 620 can be in the form of a safety shield member (structure) or can be in the form of a shied assembly formed of several parts that in combination shield the needle 101 and move in the manner described herein.

The safety shields 610, 620 are preferably biased so as to assume the desired position as the device 100 is used in the manner described herein. More specifically and according to one exemplary embodiment, the safety shield 610 has a structure that surrounds the suturing needle 101 so as to prevent easy, direct access thereto. The illustrated safety shield 610 includes a pair of side supports 612, 614 with a bottom support extending therebetween and containing an opening (slot or notch) to permit the suturing needle 101 to pass therethrough as the suturing needle 101 moves relative to the safety shield 610. As shown, the safety shield 610 is preferably a simple structure and therefore, the side supports 612, 614 can be substantially hollow and include openings formed therein. The bottom support also serves to space the two side supports 612, 614 apart from one another.

The safety shield 610 is biased with a biasing member, such as a spring, to thereby direct the safety shield 610 to an initial rest position by means of the biasing force. However, when a sufficient force is applied to the safety shield 610, the biasing force is overcome and the shield can be moved in the other direction. For example, when the safety shield 610 is brought into contact with the tissue 10, the contact with the tissue drives the safety shield 610 against the biasing force.

The illustrated safety shield 620 includes a pair of side supports 622, 624 with a bottom support extending therebetween and containing an opening to permit the suturing needle 101 to pass therethrough as the suturing needle 101 moves relative to the safety shield 620. As shown, the safety shield 620 is preferably a simple structure and therefore, the side supports 622, 624 can be substantially hollow and include openings formed therein. The bottom support also serves to space the two side supports 622, 624 apart from one another. In one embodiment, a tab 625 can be provided between the side supports 622, 624 and serves to block contact with the sharp end 103 of the needle 101. The tab 625 represents a physical structure that lies adjacent the sharp end 103 and thus effectively blocks the user from lateral access to the sharp end 103.

In one embodiment, at least one of the safety shields 610, 620 rotates relative to the handle (e.g., the cam shaft 340) when the device 100 is pressed with sufficient force against the patient's tissue. During the operating state of the device 100 when the device 100 and the safety shield mechanism 600 are rotated, the suturing needle 101 is progressively and safely exposed such that it can penetrate the patient's tissue 10. The various positions of the suturing needle 101 and safety shield mechanism 600 are described in more detail below. In the illustrated embodiment, the second shield 620 also rotates relative to the handle and relocates to the needle exit location of the patient's tissue 10 in order to protect the user from the sharp end 103 of the needle 101.

Each of the illustrated first and second safety shields 610 is biased with a biasing member, such as a spring, to thereby direct the safety shield 610 to an initial rest position by means of the biasing force. However, when a sufficient force is applied to the safety shield 610, 620, the biasing force is overcome and the safety shield(s) moves.

The shields 610, 620 are merely exemplary and the shields can take any number of different forms so long as they perform the intended function. For example, the shields can be constructed from a frame-work of formed wire or plastic and can be formed of one or more components and its rotation may be constrained by a spring or other suitable means as shown. Further, the spring element may be integral to the framework, e.g., a wire form constructed of spring tempered steel or nickel titanium alloy which possess substantial elasticity. It features a spring bias that predisposes the shield towards covering the needle point when the device is in its ready to penetrate configuration.

In one aspect of the present invention, each of the handle, the needle transfer mechanism 400, the safety shield mechanism 600 rotates about the same common axis, namely, the axis defined by the cam shaft 340. As a result, the safety shields 610, 620 are coupled to the cam shaft 340 in a rotatable manner. It will be understood that the above arrangement is merely exemplary in nature and that one or more of the above structures can pivot (rotate) about a different axis (such as a different parallel axis).

Other features and the suturing operation (technique) of the device 100 are now discussed with reference to FIGS. 1-7E. FIGS. 7A-7E eliminate a number of the inner components of the device 100 for sake of simplicity and these figures are generally presented to show the various positions of the handle, the needle shield mechanism 600 and the needle transfer mechanism 400.

Figure 7A:
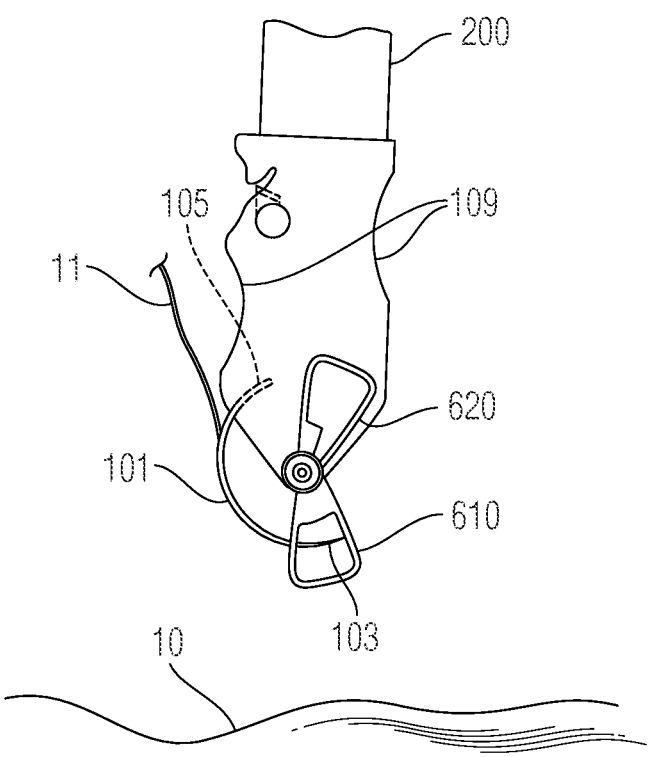
FIG. 7A is a side elevation view of the device in a first position illustrating a safety shield mechanism for shielding a suturing needle.

FIG. 7A shows the device 100 in an initial (first) position in which the handle is held in a substantially vertical position with the actuator 200 extending upward toward the user so as to be freely accessible. The needle 101 is positioned within the device 100 such that the point 103 of the needle 101 is positioned in a generally perpendicular orientation to the target tissue 10. This orientation is favorable for tissue penetration by the needle although shallower approach angles to the target tissue could be sufficient for penetration. The spring loaded safety shields 610, 620 protect the user from accidental NSIs. As shown, in this position, the first safety shield 610 surrounds the sharp tip 103 of the needle 101, thereby protecting the user. As discussed in more detail below, the opposite blunt end 105 of the needle 101 is securely grasped and held by the needle transfer mechanism 400 and in particular, is held by the first needle gripper 410. The second needle gripper 420 is in a stand-by position awaiting the needle transfer action once the actuator is activated.

Figure 7B:
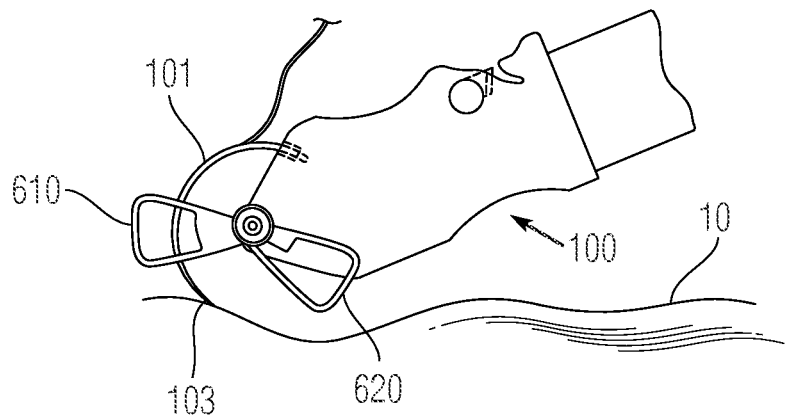
FIG. 7B is a side elevation view of device in a second position in which the device, including the safety shield mechanism, has been rotated and the suturing needle is in position for penetrating tissue.

FIG. 7B shows rotation of the handle (about the cam shaft 340) relative to the tissue 10 to effectuate the advancement of the suturing needle 101 into and through the tissue 10. It will be noted that in this second position, the suturing needle 101 is still held by the first needle gripper 410. In addition, the safety shield mechanism 600 rotates so as to position the safety shields 610, 620 in positions against the tissue 10 but still in positions to shield the needle 101. In particular, as the handle is rotated (toward the right in FIG. 7A), the safety shields 610, 620 rotate in the position as shown. As mentioned previously, in this embodiment, both the handle and the safety shields 610, 620 rotate about the cam shaft 340 to position shield 610 at a location at which the needle 101 enters the tissue 10 and shield 620 is positioned at a location in which the needle 101 exits the tissue after passage therethrough for protecting the user.

In the position of FIG. 7B, the sharp tip 103 is located immediately adjacent the tissue 10 and is ready for advancement therein. One will appreciate that compared to FIG. 7A, the handle has been rotated to assume a first acute angle relative to the tissue 10. To assume this position, the user simply rotates the handle to this angled position relative to the tissue 10.

From the position of FIG. 7B, the user rotates the handle in a direction that causes the needle 101 to be progressively driven into the tissue 10. The needle 101 is progressively and safely exposed as it penetrates the patient's tissue 10.

Figure 7C:
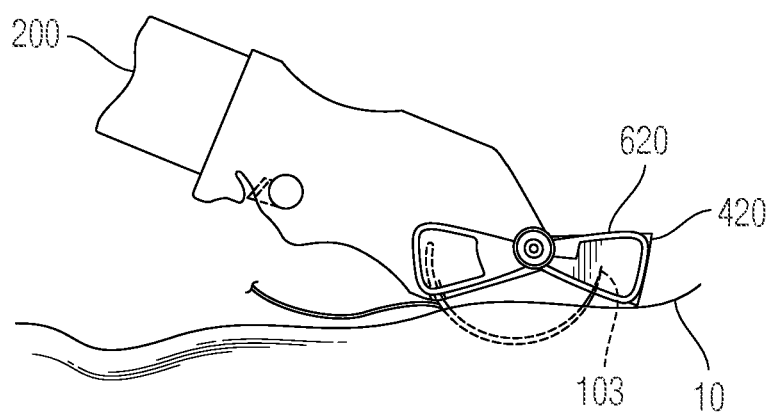
FIG. 7C is a side elevation view of device in a third position in which the device has been further rotated and the suturing needle passes through the tissue and is captured by the needle transfer mechanism.

In FIGS. 7A-7C, the handle is rotated toward the left to cause advancement of needle 101. The handle is thus rotated from the acute angle of FIG. 7B to another acute angle shown in FIG. 7C.

Of note, during this needle advancement and during entry of the needle into the tissue 10, the needle 101 is held by the first needle gripper 410.

The construction of the device 100 and arcuate shape of the needle 101 is such that this rotation of the handle causes the needle 110 to likewise travel within an arcuate path and be driven into and through tissue and then subsequently exit the tissue 10 at another location.

FIG. 7C generally shows the movement of the needle transfer mechanism 400 to capture and extract the needle 101 after the needle 101 passes through the tissue 10 by means of a needle transfer from the first gripper 410 to the second gripper 420. To transfer the needle 101, the actuator is activated by moving the actuator body 200 in a downward direction to cause rotation of the second gripper 420 to a needle receiving position at which the second gripper 420 can receive the sharp end 103 of the needle 101. In this needle receiving position, the second gripper 420 is also in an open position to permit reception of the needle 101. The second gripper 420 thus rotates downward (about cam shaft 340) towards the tissue 10 and the needle 101. At the bottom of the actuator stroke, the needle 101 is captured by the second gripper 420 and is immediately released by the first needle gripper 410. The specific actions and operation of the needle transfer mechanism 400 are described in more detail below with reference to FIGS. 1-6 and 8A-8F.

Figure 7D:
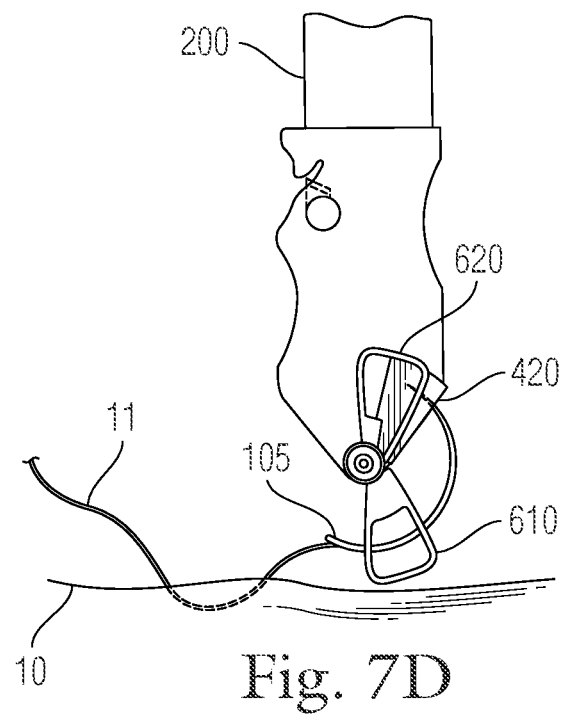
FIG. 7D is a side elevation view of the device in which the device is further rotated and the needle transfer mechanism is activated to extract the suturing needle from the tissue.

The actuator is then released and the drive (return) mechanism 225 causes the actuator body 200 to return to the rest position (actuator body 200 moves upward to the initial, rest position). While, the illustrated drive (return) mechanism 225 is a spring based system, it will be understood that other types of return mechanisms can be used to apply a force to the actuator body 200 to return the body 200 to the initial rest position. As the actuator body 200 resets itself and returns to this position, the second gripper 420 is also likewise returned to its original position (in which the second gripper 420 is contained within the handle housing). This movement of the second gripper 420 extracts the captured needle 101 from the patient's tissue 10. As shown in the position of FIG. 7D, the first gripper 410 is in a stand-by position and the blunt end 105 is free thereof. One will understand that the device 100 can be configured to employ an additional actuator stroke to extract the needle 101. Regardless of the method, the needle 101 is now free from the patient's tissue and the suture 11 has penetrated the tissue 10. While the illustrated embodiment shows the actuator body 200 as a proximally configured assembly, the actuator can equally be in the form of a side-mounted button that the user can operate with his or her palm, finger or thumb.

Figure 7E:
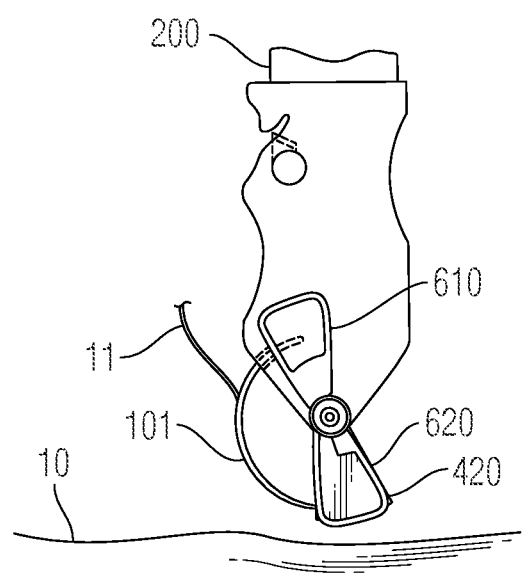
FIG. 7E is a side elevation view of the device in which the needle transfer mechanism is activated to return the needle to an initial position, thereby allowing the user to deliver another suture to the patient.

Turning now to FIG. 7E, to reset the needle transfer mechanism 400 and move the needle 101 back to the first gripper 410, the actuator is once again activated as by pressing the actuator body 200 for returning the needle 101 back to the original position within the device 100. The user has the option to cut the suture 11 at this point in time. As shown in FIG. 7E, the actuator body 200 is depressed and the second gripper 420 is moved to a distal location relative to the handle (the needle tip 103 remains shrouded by the second gripper 420). The first gripper 410 is moved into an open position thereof, thereby allowing the suture needle 101 to be received therein. The second gripper 420 opens to allow release of the suturing needle 101 to the first gripper 410.

As part of this actuator stroke, the user releases the actuator body 200 and the mechanism 225 causes a return force to be generated and thereby move the actuator body 200 back to the rest position. As the actuator body 200 is released, the first gripper 410 moves to its closed position, thereby grasping the suturing needle 101 within the first gripper 410 (i.e., the needle 101 has been returned to the original needle position). The release of the actuator body 200 causes the second gripper 420 to rotate back to the original position.

The needle transfer mechanism has thus completed its cycle at this point in that the suturing needle 101 is first transferred from the first gripper 410 to the second gripper 420 to pass the suturing needle 101 through and extract it from the tissue 10 and then the needle 101 is transferred back to the first gripper 410 to allow additional suturing to occur as shown in FIGS. 7A-7E. Once the suturing needle 101 is returned to the original position (see FIG. 7A), the user can deliver a second suture 11 to the patient. The stitches can be of a continuous type or interrupted.

As shown in FIGS. 7A-7E, throughout the entire operation of the device 100, the sharp needle end (tip) 103 of the needle 101 is covered by at least one of the safety shields 610, 620, shrouded by the second gripper 420, or embedded in the patient's tissue 10. At no time is the user exposed to the needle point (end 103). This is one of the advantages of the device 100.

FIGS. 1-6 and 8A-8F show the inner working parts of the device 100 in the various operating positions that are shown in FIGS. 7A-7E. In some of the figures, the safety shield mechanism 600 has been removed for purposes of clarity and in other figures, other components have been removed from view for clarity purposes and to allow other components to be seen. As discussed previously, the exemplary first and second grippers 410, 420 are of a reciprocating nature in that each can move between an open position (needle receiving position) and a closed position (needle grasping position).

Figure 8A:
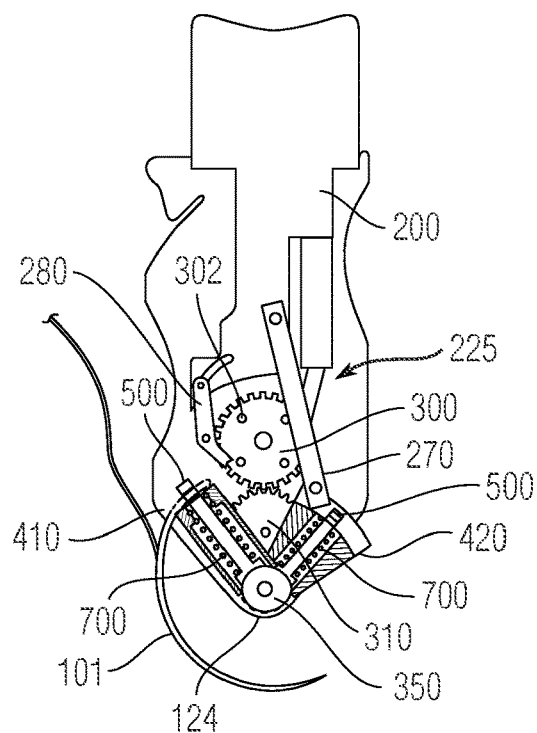
FIG. 8A is a side elevation view of inner components of the device in an initial position in which the suturing needle is ready for delivery to the patient.

FIG. 8A shows the inner components of the device 100 in the initial rest position. In this position, the needle 101 is grasped by the first gripper 410 and is free of the second gripper 420. The pin 500 associated with the first gripper 410 is biased inward towards the cam shaft 340 and a proximal portion 105 of the needle 101 is disposed within the notch 510 of the pin 500. The biased nature of the pin 500 in this position causes the needle 101 to be captured by the pin 500 within the notch 412 of the first gripper 410. In this position, the needle 101 is effectively grasped by the first gripper 410 which as mentioned earlier is fixed relative to the handle. The (drive) return mechanism 225 is likewise shown in the non-actuated state since the actuator body 200 is in the rest position.

Figure 8B:
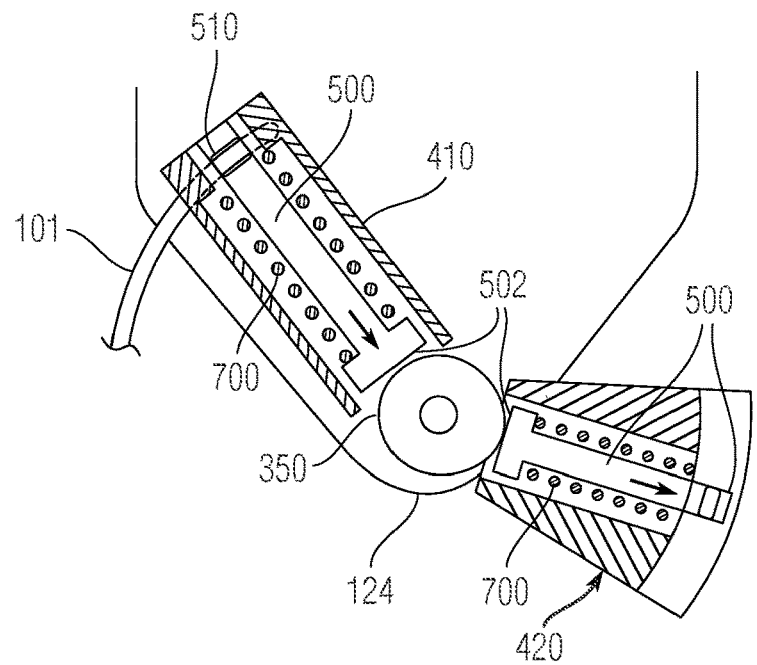
FIG. 8B is a close-up cross-sectional view of a needle transfer mechanism according to one embodiment and in a needle transfer position in which the suturing needle can be shuttled.

FIG. 8B is a close-up view of the cam shaft 340 and in particular, the cam member 350 thereof in relation to both of the first and second pins 500. The cam member 350 engages both of the pins 500 and in this initial position, the pin 500 associated with the first gripper 410 is shown being biased in a direction toward the cam shaft 340 (as indicated by the arrow). This position of the cam member 350 causes the pin 500 associated with the second gripper 420 to be directed outwardly in a direction away from the cam shaft 340 since the force of the cam member 350 against the pin 500 overcomes the biasing force of the pin 500 associated with the second gripper 420.

As the actuator body 200 is depressed, the cam shaft 340 rotates (cam member 350 likewise rotates) and the pins 500 are translated away from and back towards the center axis of the cam shaft 340. When either of the pins 500 is translated away from the cam shaft 340, it releases the suture needle 101 and when either of the pins 500 is translated towards the cam shaft 340, the gripper grasps and holds the suturing needle 101. One will appreciate that the needle transfer mechanism 400 in combination with the cam action of the cam member (body) 350, the suturing needle 101 is gripped by one of the first and second grippers 410, 420 at all times and cannot become free from the device 100. The needle transfer mechanism 400 according to the present invention provides safety to the user and others that may come into contact with the device 100. In addition, this feature is the mechanism 400 that enables the needle 101 to be shuttled from one gripper 410, 420 to another in order to facilitate the suturing process in a controlled manner and based on normal movements of the user, such as traditional wrist rotation.

Although the embodiment shown in the figures that the needle gripping action occurs when the pins 500 alternatively translate towards the center axis of the cam shaft 340 and the needle release action occurs when the pins 500 alternatively translate away from the center axis of the cam shaft 340, one of skill in the art will understand that the directions of the needle grasping (clamping) and releasing actions can be reversed with a modification of the relevant structures.

Figure 8C:
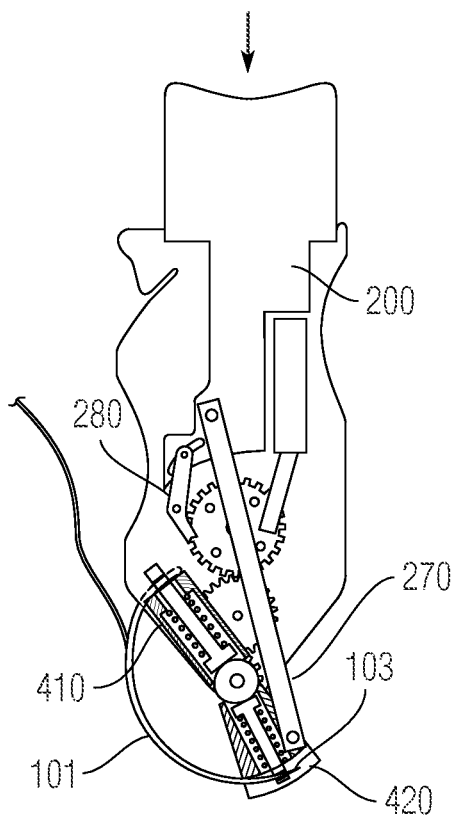
FIG. 8C is a side elevation view of the device showing the needle transfer mechanism is activated and a portion of the needle transfer mechanism captures the suturing needle.

Now turning to FIG. 8C, the actuator body 200 has been depressed to activate the actuator and the second gripper 420 engages the sharp end 103 of the needle 101. More specifically, as the actuator body 200 is depressed, the actuator body causes the link arm 270 which is coupled thereto to move downward and at the same time the drive (return) mechanism 225 stores energy due to the biasing member (e.g., a spring)(not shown) associated with the mechanism 225 being compressed. Since the link arm 270 is coupled at its distal end directly to the second gripper 420 (i.e., the body 440) and the second gripper 420 is directly coupled to the cam shaft 340, the movement of the actuator body 200 is directly translated into rotation of the second gripper 420 and in this case, the movement of the second gripper 420 is a rotation about the cam shaft 340. The gear 300 is driven by the movement of the actuator body 200 and this causes rotation of the other gears and this results in rotation of the cam member 350 since the third gear 320 is directly coupled to the cam shaft 340. This movement (rotation) of the cam member 350 causes the reciprocating motion of the pins 500 that is described above. This reciprocating movement causes the pins 500 to selectively open and close depending upon the position of the cam member 350 and this action in combination with the controlled movement of the second gripper 420 provide a means for effectively transferring the suturing needle 101 from one gripper to another gripper depending upon the particular operating stage of the present device 100. As mentioned above, the pawl 280 and ratchet 290 allow the gears 300, 310, 320 to rotate only in one direction.

FIG. 8C thus shows the needle transfer from the first gripper 410 to the second gripper 420 after at least the distal sharp end 103 of the suturing needle 101 has exited the tissue 10. The rotation and position of the cam member 350 at the time of needle transfer is such that the first gripper 410 opens to allow transfer of the suturing needle 101 from the first gripper 410 to the second gripper 420 and the second gripper is initially open to receive the sharp end 103 of the suturing needle 101. The exemplary positions of the grippers 410, 420 at the time of the needle transfer are shown in FIG. 8C.

Figure 8D:
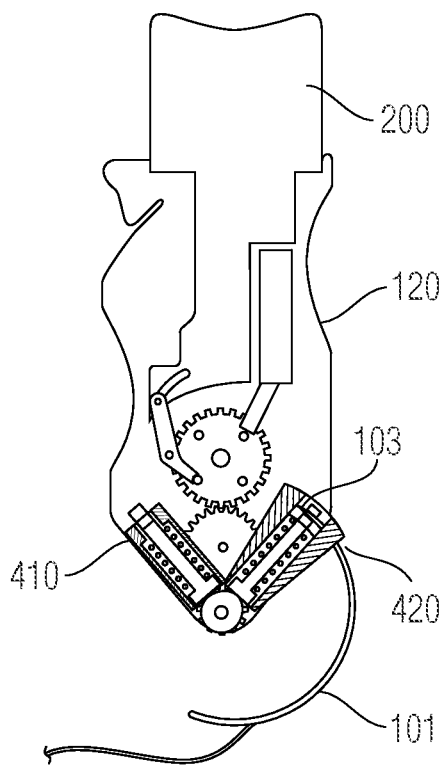
FIG. 8D is a side elevation view of the device showing a release of the needle transfer mechanism, thereby causing the captured suturing needle to be extracted from the tissue.
Figure 8E:
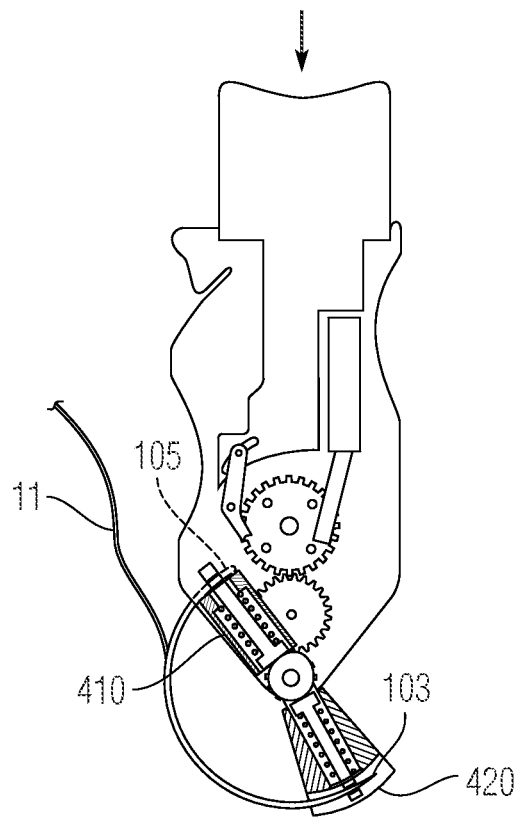
FIG. 8E is a side elevation view of the device showing subsequent activation of the needle transfer mechanism to return to the suturing needle to the initial position.

FIG. 8D shows the release of the actuator body 200 and the drive (return) mechanism 225 causes the actuator body 200 to move in a direction away from the needle transfer mechanism 400 (i.e., it resets the actuator body 200 to the initial rest position). The release of the actuator body 200 causes the second gripper 420 to rotate back towards the handle (i.e., back to the initial rest position of the second gripper 420). This movement (rotation) of the second gripper 420 causes extraction of the needle 101 from the tissue 10 since the suturing needle 101 is grasped by the second gripper 420 and remains free from the first gripper 410. In this retracted position of the second gripper 420, the second gripper 420 can be at least substantially contained within the handle. This position is also shown in FIG. 7D. As mentioned above, the suture 11 can be cut at this time.

As mentioned before, to return the suturing needle 101 to the original, initial position in which the suturing needle 101 is grasped by the first gripper 410 and is ready for subsequent advancement into and through the tissue 10, the user activates the actuator by depressing the actuator body 200 again (to cause further cycling of the needle transfer mechanism 400). Depressing the actuator body 200 causes movement of the link arm 270 as described above and causes movement of the return mechanism 225 (to store energy) and these movements result in the second gripper 420 moving (rotating about the cam shaft 340) in a direction toward the tissue 10 away from the handle. Since the suturing needle 101 is securely grasped by the second gripper 420 during this movement, the suturing needle 101 is also moved back to its original position. This movement of the second gripper 420 moves the needle 101 along an arcuate path and delivers the blunt end 105 of the needle 101 to the first gripper 410 and also results in the pin 500 associated with the first gripper 410 moving to the open (needle receiving) position, thereby allowing the blunt end 105 of the needle 101 to be received within the notch 412 and the notch 510 of the pin 500. At the same time, at the end of the actuator stroke, the pin 500 of the second gripper 420 moves to the open position, thereby allowing release of the needle 101.

Figure 8F:
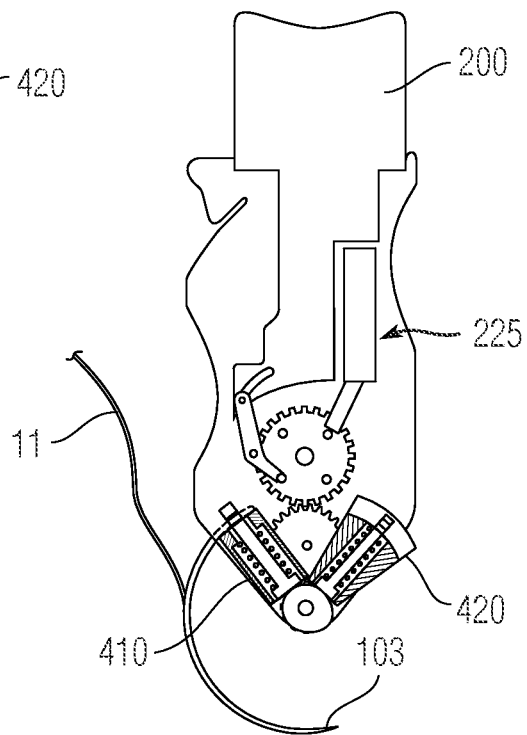
FIG. 8F is a side elevation view of the device showing a release of the needle transfer mechanism to return the needle transfer mechanism to return to the initial rest position.

FIG. 8F shows the release of the actuator body 200 and the return of the second gripper 420 to its original, rest position. Once the actuator body 200 is released, the drive (return) mechanism 225 drives the actuator body 200 (by releasing its stored energy) to its initial rest position and since the second gripper 420 has released the suturing needle 101, the needle 101 is grasped by only the first gripper 410 and the second gripper 420 (which is free of the needle 101) rotates back towards the handle to its original position.

One alternative embodiment of the present device, which extracts the needle 101 from the patient's tissue with a rotational handle motion, is configured with a second gripper that linearly approaches and grasps the needle 101 via the partial depression of the actuator, and as the actuator depression continues, the motion of the second gripper abruptly transitions from linear to rotational and the needle 101 is rotatably extracted from the patient's tissue. A subsequent actuation of the plunger rotates the needle back to its origin and returns the second gripper to its original position.

It will be appreciated that other needle transfer mechanisms can be used to shuttle the suturing needle 101 from one location and from one gripping member to another location and another gripping member.

Figure 9A:
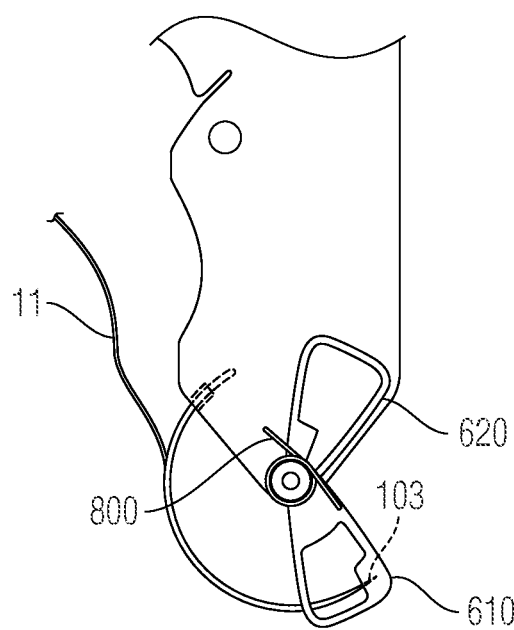
FIG. 9A is a front elevation view of the distal end of the device showing a safety shield mechanism according to one exemplary embodiment according to one embodiment.
Figure 9B:
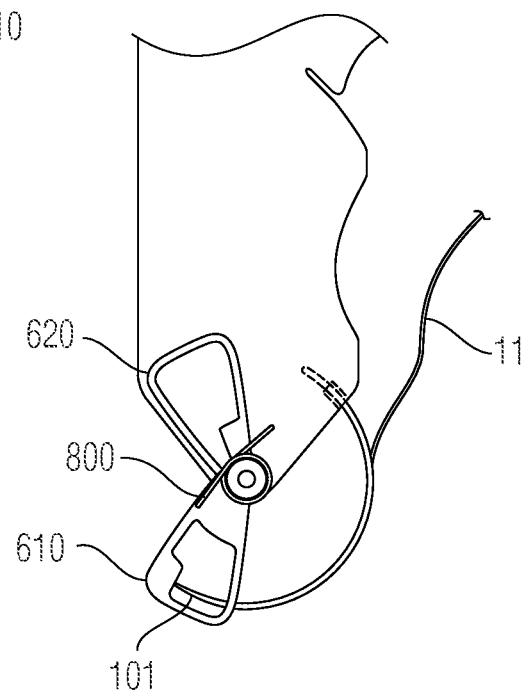
FIG. 9B is a rear elevation view of the distal end of the device showing the safety shield mechanism.

FIGS. 9A and 9B illustrate front and back views of a two piece safety shield that can be used with the device 100 for shielding the suturing needle 101 over its range of motion in the manner described herein. The first safety shield 610 is rotatably coupled to the device handle by shaft (axle) 340 and a torsion spring 800 or other suitable means. The first safety shield is also rotatably coupled to the second safety shield 620 by a torsion spring or other suitable means. Thus, two springs 800 are used in this design. The spring-loaded engagement between the first safety shield 610 and the handle permits the user to rotate this shield 610 relative to the handle and to safely penetrate the patient's tissue with the needle. The spring-loaded engagement between the first safety shield 610 and the second safety shield 620 forces the latter shield to follow the rotational path of the former while simultaneously providing flexibility between the two shields 610, 620. This flexibility enables the shields 610, 620 to adapt to variable topographies (e.g., tissue, catheter hubs) and still protect the user from the point of the needle throughout the operation. More specifically, the shields 610, 620 contact the tissue which applies a force that counters the biasing force of the shields 610, 620, yet the biasing force of the shields 610, 620 drives the shields 610, 620 into engagement with the tissue and as shown, when in contact with the tissue 10, the shields 610, 620 rest thereagainst at two different (opposite) locations along the tissue 10.

In another contemplated embodiment, the shields 610, 620 can be constructed as a single piece that features an integral flexible portion that allows for a similar adaptation to variable topographies.

An additional feature of the safety shield(s) 610, 620 provides the user with the ability to precisely deliver the needle 101 to the patient. This feature may be a protrusion on one of the shields 610, 620 that, for example, aligns the needle to the suture hole of a catheter hub. This feature may also be a ring, semi-circular structure, or visible mark on the shield that helps the user to more clearly visualize the desired needle penetration and/or exit sites upon the tissue. In particular, when the second shield 620 seats against tissue, the user can immediately be aware of where the sharp end 103 of the needle 101 will exit the tissue 10.

Figure 12:
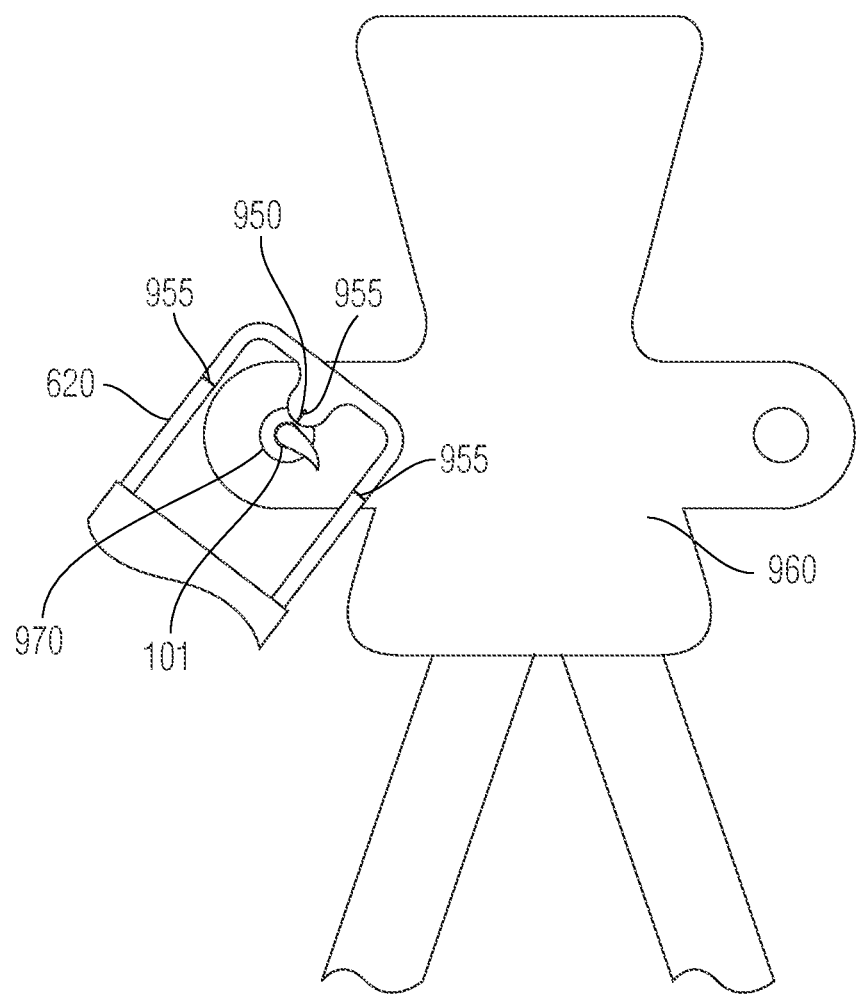
FIG. 12 is a top plan view of a portion of one safety shield showing an alignment feature thereof being used in an exemplary application.

More specifically, FIG. 12 shows one exemplary alignment feature that can be part of at least one or both of the safety shields 610, 620. As shown in the top plan view of FIG. 12, the alignment feature can be in the form of a protrusion 950 that extends inwardly from a frame of the shield 610, 620. The protrusion 950 serves as a tool to indicate to the user the location at which the needle will pass through the shield 610, 620 as it is either being driven and advanced into the tissue (as in shield 610) or when it is exiting the tissue and is received within the shield 620. The alignment feature 950 preferably includes alignment indicia 955 to show the user the precise location at which the needle 101 passes through the respective shield 610, 620. In the illustrated embodiment, the indicia 955 consists of three separate markings, namely two markings on the sides of the shield's frame and one marking at the end of the shield's frame (however, less than or greater than 3 markings can be used). The two markings on the sides are opposite one another and therefore, define a first alignment line and the single end marking also is used to define a second alignment line that is perpendicular to the first alignment line. The point (area) at which the first and second alignment lines intersect represents the point (area) at which the needle 101 will pass through the shield. The alignment indicia 955 can be integral to the shield (i.e., formed in a common mold operation) or can be added in a secondary operation, such as pad printing, adding a decal or laser etching.

FIG. 12 shows the shield 620 since in this view, the needle 101 has passed through the tissue and is being passed through a suture hole 970 that is formed in a catheter hub of a catheter 960 for placement and securement on the tissue of the patient using the suture. The illustrated catheter hub includes a main catheter tube and a pair of extension tubes shown partially in the figure. As a result, the alignment feature 950 associated with second shield 620 serves to indicate to the user the location of the needle tissue-exit site. However, the first shield 610 also preferably includes the alignment feature 950 for indicating to the user the location at which the needle 101 passes through the first shield 610 prior to entering the tissue, etc. This allows the user to align the device properly relative to a target by positioning the shield 610 at the desired location at which the needle 101 will be driven into the target. In the example of FIG. 12, the alignment feature 950 of the first shield 610 is aligned with one suture hole 970 of the catheter hub and then the needle 101 is advanced and passes through the first shield 610 and through the suture hole 970 before entering the tissue.

It will be understood that the alignment feature can be used to align the shields 610, 620 with target points on tissue itself in applications not involving a catheter (i.e., applications in which tissue is directly sutured).

Figure 13:
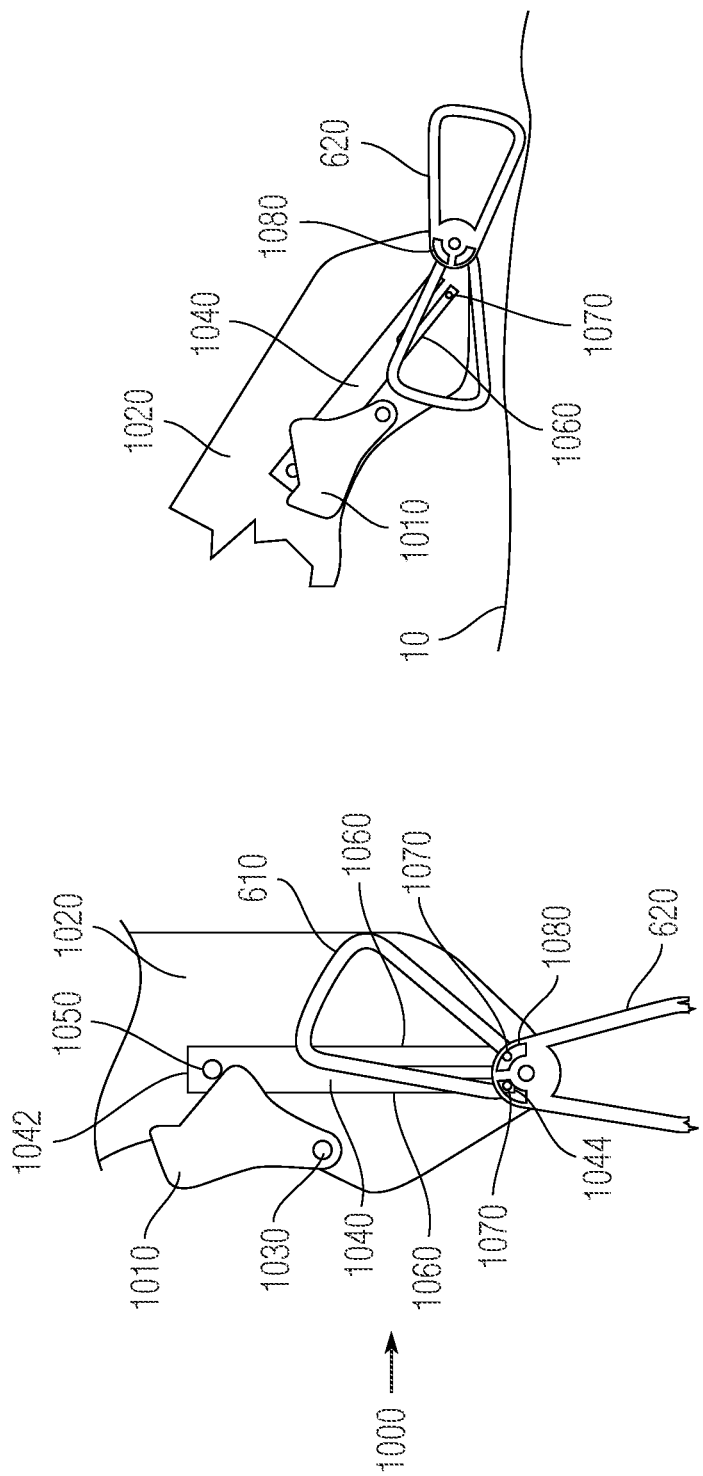
FIG. 13A is a side elevation view of the inner components of a lockout feature for use in the suturing devices of the present invention, wherein the lockout feature is shown in the locked position.
FIG. 13B is a side elevation of the lockout feature of FIG. 13A is a deactivated (unlocked) position.
Figure 14:
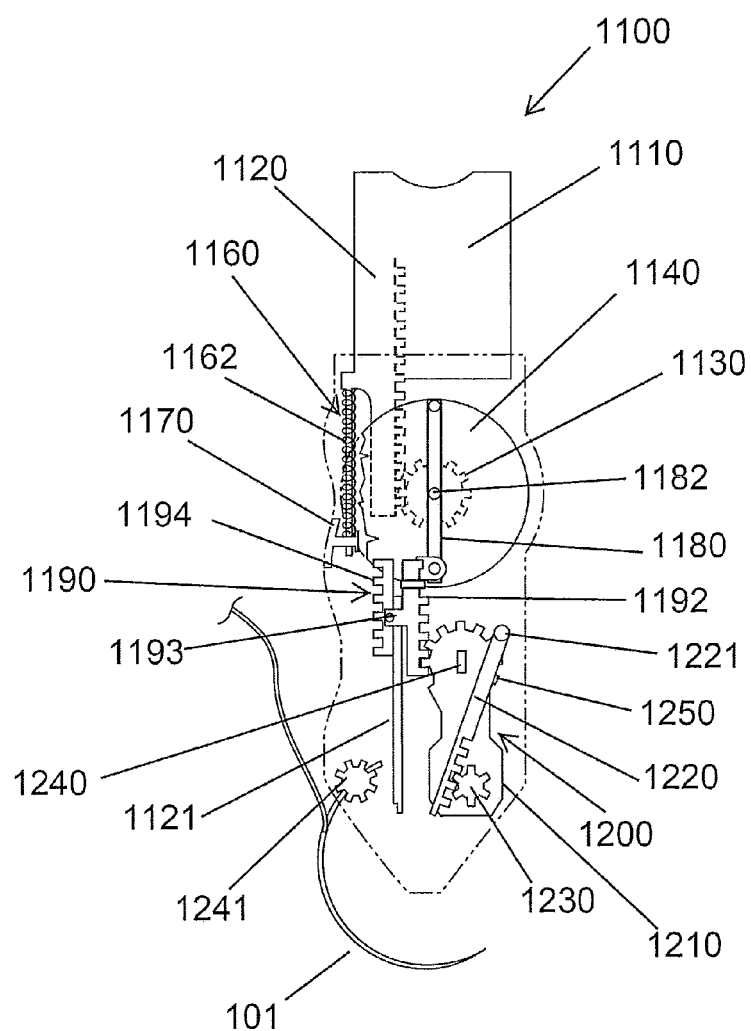
FIG. 14 is side elevation view of the inner components of a suturing device in accordance with another embodiment of the present invention, wherein an actuator of the device is shown in a first (home) position.
Figure 15:
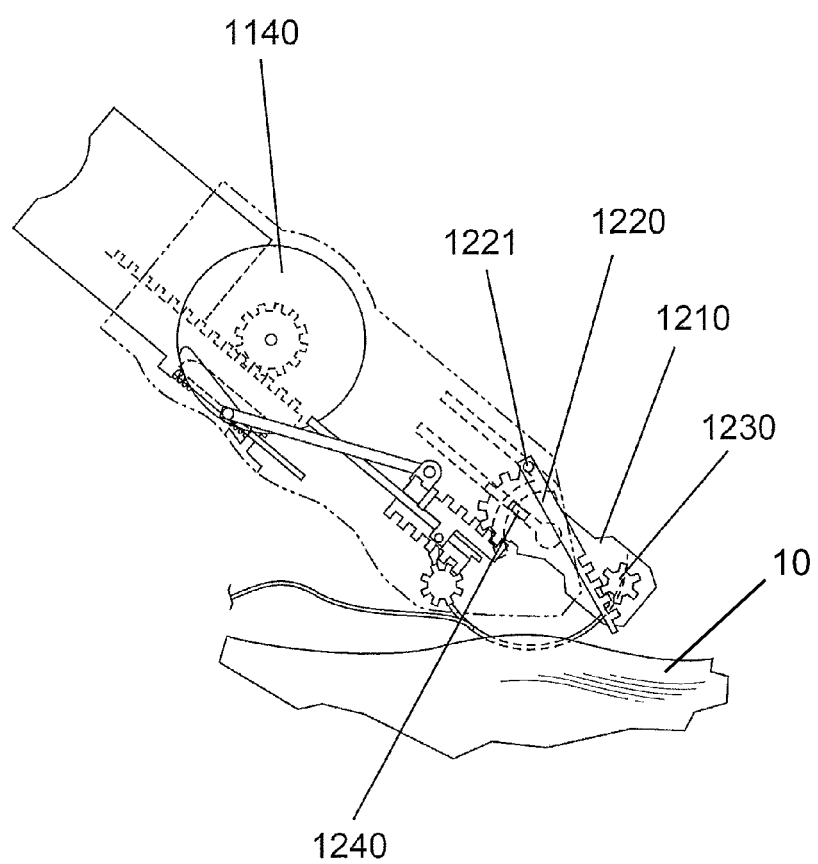
FIG. 15 is a side elevation view of the suturing device of FIG. 14 with the actuator being shown in a partial stroke position.

Additional safety can be provided to the user through a safety shield lockout feature, which prevents the shield(s) from rotating and thereby exposing the needle to the user, even when pressure is exerted upon the shield(s). FIGS. 13-15 illustrate a lockout mechanism 1000 in accordance with one embodiment of the present invention. The lockout mechanism 1000 is designed to prevent the user from accidentally exposing the needle and obtaining an NSI. The lockout mechanism 1000 can take the form of a user-actuated button, lever, slide, or other similar means and a connecting element that couples the actuation means and the safety apparatus. The button causes the connecting element to lock and unlock the apparatus in a variety of ways. Examples of these means include tongue and groove, intermeshing gears, friction and interference fits, inclined panes, cantilever, and screws. In each of these methods, the connecting element restricts the movement of the apparatus, and therefore, the exposure of the needle until the user actuates the button to release the apparatus. A lockout mechanism in the form of a slideable button (FIG. 13A) engages one or both of the safety shields 610 and 620 such that the shields 610, 620 will not expose the sharp distal point 103 of the needle 101 to the user. When the button is pressed and unlocks safety shields 610 and 620, the suturing device and safety shields can be rotated such that the needle 101 is progressively and safely exposed in order to penetrate the patient's tissue in the manner described herein with reference to the various suturing devices of the present invention.

FIG. 13A depicts a magnified view of the distal end of a suturing device according to any one of the embodiments described and illustrated herein. In other words, the lockout mechanism 1000 can be incorporated into any of the suturing devices disclosed herein. The lockout mechanism 1000 consists of a lockout button (actuator) 1010, which is pivotally attached to the handle body 1020 by pin 1030, and a lockout linkage 1040 which can be in the form of an elongated beam like structure having a first (proximal) end 1042 and an opposing second (distal) end 1044. It will be understood that the actuator 1010 is the same as actuator 110 and the body 1020 is the same as body 120 when the lockout mechanism is employed in device 100. The linkage 1040 slides generally longitudinally within a channel in the handle body and alternatingly between locked and unlocked positions of safety shields 610 and 620. The linkage 1040 has an attached drive pin 1050 at the first end 1042, legs 1060, and feet 1070 extending outwardly from distal ends of the legs 1060. A spring (not shown) biases the linkage 1040 distally and locks shield 620 from rotating. When button 1010 is pressed, its ramp-like surface guides the drive pin 1050 proximally, which in turn extracts the beam feet 1070 from lock notches (openings) 1080 in safety shield 610 and allows the shield 610 to rotate. Once the shield 610 begins to rotate, the beam feet 1070 cannot reengage the shield 610 until the shield returns to its ready mode position and the lockout button 1010 is released.

Looking now at FIG. 13B, the suturing device has been manipulated such that the lockout mechanism 1000 has been deactivated (unlocked), the shields 610 and 620 have rotated, the needle (not shown) has entered and exited the patient's tissue 10. In this deactivated or unlocked state, the shields 610, 620 can rotate.

Once the suturing device is drawn away from the patient and the suture remains in the patient's tissue 10, the lock out button 1010 can be released and returned to its default position and safety shields 610, 620 are restricted from rotating. The suturing device has thus been placed back into the locked position.

It will be understood that the illustrated lockout mechanism is merely exemplary in nature and other mechanical structures can be provided to achieve the intended lockout functionality.

Figure 10:
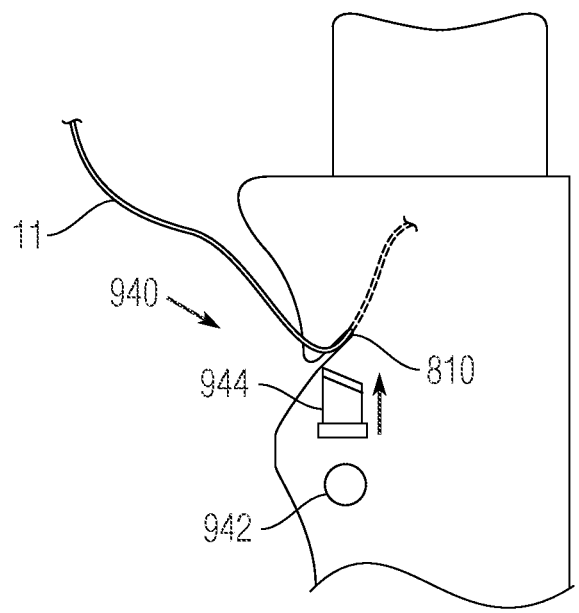
FIG. 10 is a partial side elevation view of the device showing an internal cutter mechanism according to one exemplary embodiment.

The device 100 also preferably includes a means for cutting the suture 11. FIG. 10 shows a suture cutter 940 that is integral to the handle would provide the user with a means to cut and trim suture during the procedure. Any number of different types of cutting members can be used and in the illustrated embodiment, the suture cutting 940 is provided within the handle. The suture cutter 940 includes a cutter guide notch or slot 810 that receives and stabilizes the suture 11.

As depicted in FIG. 10, the cutter is an internal dynamic shearing apparatus, i.e., scissors or slideable blade(s), that would require the user to press or slide a button 942 in order to activate the blade 944 to cut the suture. Any number of different types of cutter actuators can be used including but not limited to the button 942 (as shown), a slide, lever or other structure that is coupled to the blade 944 such that movement of the actuator is translated into movement of the blade 944 sufficient to generate a cutting force that cuts the suture 11 contained within the notch 810.

Figure 11:
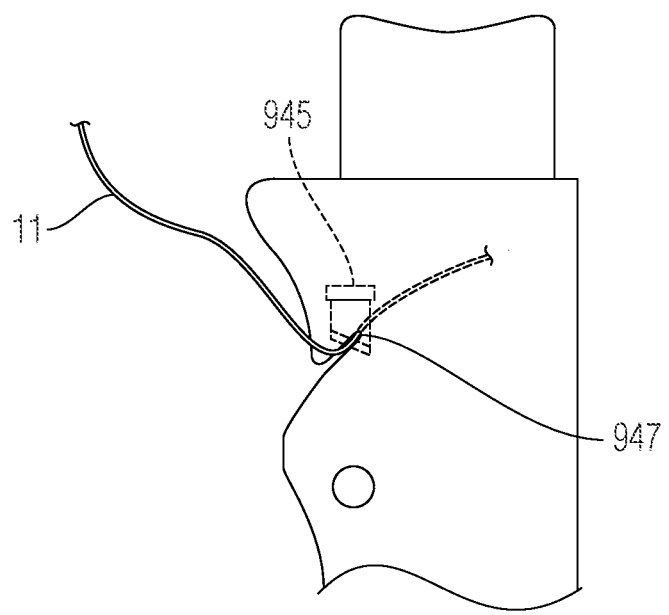
FIG. 11 is a partial side elevation view of the device showing an internal cutter mechanism according to another embodiment.

The button (actuator) 942 is connected to a means that translates the blade 944 across the suture 11. It will be appreciated that the blade 944 is constrained by a set(s) of parallel faces (distal and proximal to the suture cutting locus) to ensure alignment of the blade as it approaches the suture, cuts the suture, and its forward stroke beyond the point of cutting. This means could be a slideable track if the button were to slide in the direction of the blade 944, or a pair of matched ramps that would convert the vertical motion of the depressed button to a horizontal motion of the cutting blade. A spring or other suitable means would return the button 942 to its original position. Further, the suture would be positioned in a notch, slot, or hole 810 on the outer surface of the housing. Alternatively shown in FIG. 11, the cutter can be a simple apparatus such as a static cutting blade 945 located near the exterior surface of the handle. The blade 945 can be affixed in a narrowing, crevice-like feature 947 that is sized so that the suture 11 can be drawn across the blade's sharp edge in order to cut it however direct access to the blade by the user is not possible due to the crevice's narrow pathway. These features would reduce or eliminate the need for the user to provide a pair of scissors for the suturing procedure.

It will therefore be appreciated that in one exemplary use and according to one exemplary design, the suturing needle 101 is manually advanced by a rotation of the handle from a first position at which the handle is at a first acute angle relative to the tissue 10 to a second position at which the handle is at a second acute angle relative to the tissue 10. The rotation (pivoting) of the handle from the first to the second positions causes the suturing needle 101 to be driven into the tissue 10 and pass through the tissue 10 to a tissue exit location at which the suturing needle 101 can be grasped and extracted from the tissue 10. To shuttle (transfer) the needle 101 between its various operating positions, the actuator is activated to cause transfer of the needle 101 from the first gripper 410 to the second gripper 420 which then actively grasps and extracts the needle 101 from the tissue. This completes one suturing action (cycle) in that the needle 101 has been driven into, through the tissue and extracted from the tissue 10. To begin a next suturing action, the needle 101 is returned (shuttled) to the first gripper 410 and assumes its original position.

The present needle transfer mechanism 400 thus provides an effective means for passing the needle 101 through the tissue 10 for suturing thereof, while at the same time, the complementary safety shield mechanism 600 shields the user from the sharp end 103 of the needle 101.

Now turning to FIGS. 14-17, a suturing device 1100 according to another embodiment of the present invention is illustrated. For clarity and simplicity, a number of components of the suturing device 1100 are not shown but are shown in the previous figures and therefore, it will be understood that the device 1100 can and preferably does include one or more of these features, mechanisms, etc. For example, the safety shields 610, 620 and suture cutter 940 have also been removed for this illustration, as their operation is detailed in other figures. Further, a number of ribs, screws, and other basic features of the body of the device are also not shown. When these features are important to the operation of the device, they will be described accordingly.

Figure 16:
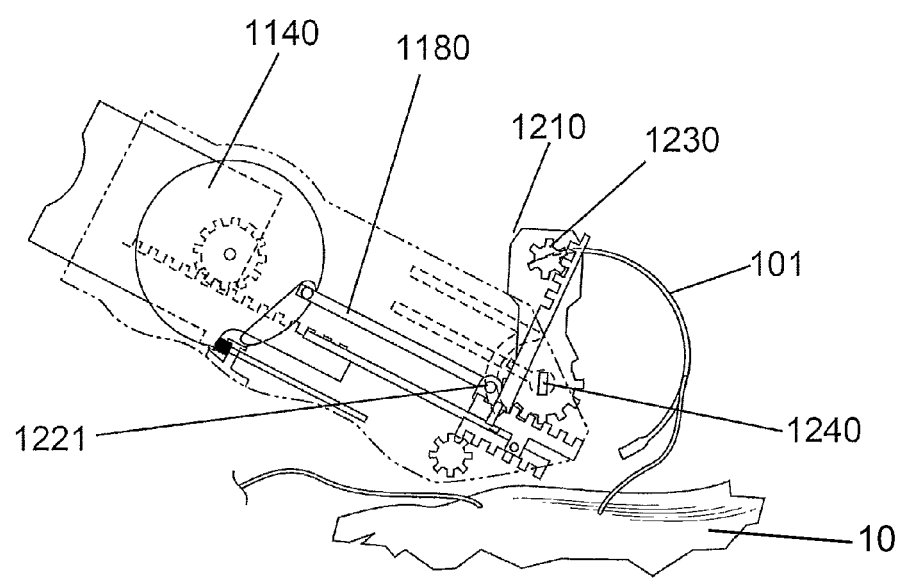
FIG. 16 is a side elevation view of the suturing device of FIG. 14 with the actuator being shown after a full stroke position.

As with device 100, the device 1100 includes an actuator 1110 the movement of which controls a number of the operative parts of the device 1100. FIGS. 14-16 depict three stages of the actuator 1110 travel (namely, home, partial stroke, full stroke positions) and the resulting movement of the device's primary internal components. The proximal end of the device is defined by the actuator 1110 which can take any number of different forms. The actuator body is such that the user can easily access and manipulate the actuator body as by pressing the actuator body downward as in the previous embodiment. The actuator 1110 includes an actuator rack 1120 which is designed to engage a main drive gear 1130 which is rotatably disposed within the housing (handle) of the device 1100.

The main drive gear 1130 in turn engages a main drive wheel 1140 which is also rotatably disposed within the housing. The connection between the main drive gear 1130 and the main drive wheel 1140 can be in the form of a one directional ratcheting or clutching mechanism. A variety of means for ratcheting or clutching may be used, including a simple ramped and spring loaded interface between the gears or a torque spring clutch type mechanism. Other types of clutches may be used instead. The net effect of the drive gear 1130 and drive wheel 1140 interaction is that on the down-stroke of the actuator 1110, the gear 1130 drives the wheel 1140, while on the subsequent up-stroke of the actuator the gear 1130 disengages from the wheel 1140 and the drive wheel 1140 therefore remains stationary.

The actuator 1110 of FIG. 14 also includes an elongated spring rod 1160, which is connected to the actuator 1110 by a suitable means, and slides through a tight-clearance bearing 1170. The spring rod 1160 is also configured to support a long compression spring 1162, which is located between the bearing 1170 and the proximal end of the actuator 1110. The spring rod 1160, bearing 1170, and compression spring 1162 together bias the actuator 1110 proximally and automatically return the actuator 1110 after each completed actuator depression. In other words, these components generate a return force for returning the actuator the rest (home) position.

The main drive wheel 1140 has an elongated reciprocating linkage 1180, which is pivotably attached to the drive wheel 1140 by a pin 1182 or other mechanism. The reciprocating linkage 1180 is further connected to a reciprocating rack assembly 1190. The reciprocating rack assembly 1190 is made up of a receiving side rack 1192 and a delivery side rack 1194. The reciprocating rack assembly 1190 and the individual racks 1192, 1194 thereof ride on a number of ribs (not shown) which are part of the handle of the suturing device 1100. The ribs are configured such that the rack motion is constrained in a single vector which is roughly parallel to the longitudinal axis of the device. A single such rib 1121 is depicted in order to illustrate the concept. The receiving side rack 1192 is connected to a receiving shuttle assembly 1200, which will be described in detail shortly.

The actuator rack 1120, main drive gear 1130, and main drive wheel 1140 are configured such that one completed actuation of the actuator 1110 rotates the drive gear 1130 and drive wheel 1040 180 degrees. In this manner a single stroke moves the reciprocating rack assembly 1190 from its proximal most location to its distal most location. A second complete stroke would return the rack assembly to its initial configuration.

The receiver shuttle assembly 1200 of FIG. 14 includes a receiver shuttle body 1210, a sliding rack 1220, and a pinion screw 1230. The pinion screw 1230, illustrated as a simple pinion gear for clarity, is essentially a simple screw with a pinion gear head. The pinion screw 1230 has a right handed thread. The sliding rack 1220 sits inside a groove in the receiver shuttle body 1210, such that sliding rack 1220 is constrained in all directions except for along the axis of the sliding rack 1220 itself. The rack 1220 and screw 1230 are mated such that the sliding motion of the rack 1220 along its track translates to a rotation of the screw, which in turn actuates the screw into or out of the page of FIG. 14.

The receiver shuttle body 1210 is an elongated structure designed to be injection or cast molded or formed using another technique. At the distal end of the receiver shuttle body 1210 a slot runs across the width of the body. The slot is positioned roughly at the center point of the thickness of the receiver shuttle body, and is configured such that a needle may fit inside the slot. The slot feature of the shuttle body extends proximally well past the pinion screw 1230. The pinion screw 1230 is threaded into a complementary hole formed in the shuttle body 1210. The hole only exists on one side of the slot and not the other, such that the motion of the screw 1230 is limited and will bottom out on the surface of the other side of the device tightened accordingly. The shuttle body 1210, slot, pinion screw 1230, and threaded hole are all configured such that the shuttle body 1210 can slide over the needle 101, which fits into the slot, and then clamped by the end of the pinion screw 1230, in a manner that is similar to a bench vise. The clamping action of the pinion screw 1230 is sufficient to tightly secure the needle 101 in the handle.

At the proximal end of the receiver shuttle body 1210 of FIGS. 14 and 15, a rectangular pin 1240 is shown, as well as a series of gear teeth 1250. As described above, the gear teeth 1250 of the receiver shuttle body 1210 are mated with the receiving side rack 1192 in the typical rack and pinion type configuration. The proximal most end of the sliding rack 1220 features a rack pin 1221. The rectangular pin 1240, which is a round pin featuring a pair of parallel, flat edges, and the rack pin 1221 both ride between a number of ribs, which together create a well defined path that allows for a controlled motion of the two parts. The exact motion of the receiver shuttle assembly 1200 and the constituent parts are best described in a later drawing. For now it is sufficient to know that the motion of the sliding rack and rectangular pin are well defined and controlled. Furthermore it is important to understand that the receiver shuttle assembly is driven by the travel of the actuator. This travel translates into the actuation of the receiver shuttle assembly 1200 by way of the main drive wheel 1140, linkage 1180, and reciprocating rack assembly 1190.

Referring to FIGS. 15 and 16, a second pinion screw 1241 is depicted near the proximal end of the needle 101. In order to differentiate the two pinion screws the second pinion screw 1241 will be referred to as being the delivery pinion screw. This pinion screw 1241 acts to clamp the proximal end of the needle 101 in the same way that the first pinion screw works to clamp the distal end of the needle 101 as described above. The pinion screw 1241 is configured such that the screw will interact with delivery side rack 1194. The delivery side rack 1194 is connected to the receiving side rack 1192 by way of a pin 1193, which extends from the receiving side rack 1192 and fits into a slot of the delivery side rack 1194. The pin 1193 can slide along the slot; however it is ordinarily biased to one direction with the aid of a compression spring (not shown).

Figure 17:
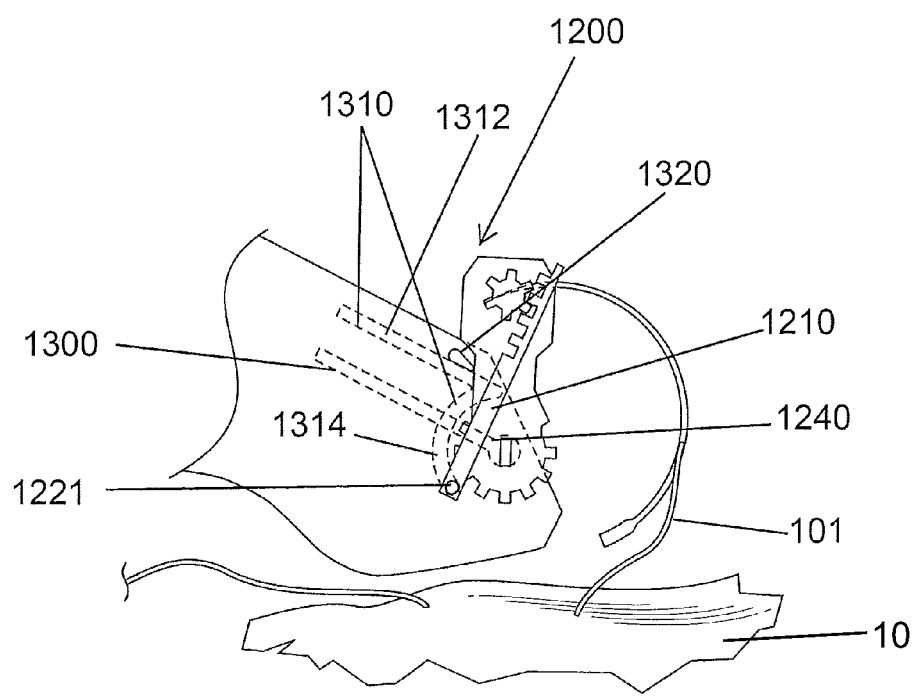
FIG. 17 is a side elevation view of the suturing device of FIG. 14 with internal guide channels (grooves) for controlling movement of the various pins employed in the suturing device.

Referring particularly to FIGS. 15-17, a simplified view of the distal end of the device has been shown. The purpose of this figure is to illustrate the path that the receiver shuttle assembly 1200 takes during the actuation of the device. As depicted, two distinct and separate paths are created by slots and ribbed features within the body of the handle. The central rectangular pin path 1300 guides the travel of the receiver shuttle body 1210. The rectangular pin 1240 of the shuttle assembly travels in a specific orientation, which is constrained by the width of the central rectangular pin path 1300. The path maintains a relatively constant width throughout its length except for the most distal region where the path changes rapidly to a full diameter, which is wider than the proximal width of the path and permits the previously constrained rectangular pin to rotate within. The practical effect is that the receiver shuttle body 1210 moves exclusively in an axial direction during specific parts of the device cycle and then rotates in while in others. It is through these movements by the receiver shuttle body that the needle is gripped, released, extracted from tissue, and returned to its origin.

Still referring to FIG. 17, a compound rack guiding path 1310 is depicted. This compound path is configured to constrain the rack pin 1221 of the receiver shuttle assembly 1200. The path has two distinct but connected sections: a linear section 1312, and an arcuate section 1314. The linear section 1312 of the path 1310 is parallel and analogous to the linear section of the rectangular pin path 1300. The relative positions of the two paths are configured such that when the rectangular pin 1240 is prevented from rotating about its axis the rack pin 1221 is only permitted to move in the axial direction within the arcuate section 1314. When the rack pin 1221 initially enters the curved (arcuate) section 1314 of the rack pin path, the rectangular pin 1240 has not yet entered the distal-most, diametral region of its respective path 1300. Next, as the user continues to depress the actuator 1110, the receiver shuttle body 1210 continues to travel linearly along its path while the rack pin 1221 is simultaneously constrained at the base of the straight section. This results in relative motion between the sliding rack 1220 and the receiver shuttle body 1210. The relative motion continues until the rectangular pin 1240 enters the distal most, diametral region of the rectangular pin path 1300. At this point, the rectangular pin 1240 is able to rotate about its axis, and this rotation in turn translates to the travel of the rack pin 1221 through the arcuate section 1314 of the rack pin path 1310. The relative motion between the sliding rack 1220 and the receiver shuttle body 1210 creates the synchronized rotation of the pinion screw 1230 that leads to it gripping the needle 101. This needle gripping action occurs prior to the rotation of the receiver shuttle body 1210 about its axis, and that enables the receiver shuttle assembly to automatically extract the needle 101 out of the tissue 10 as the actuator 1110 is depressed. At this point, the needle 101 and suture have penetrated and exited the patient's tissue 10.

A ratchet mechanism 1320 is designed to prevent the receiving shuttle rack pin 1221 from moving into the linear section 1312 of its path 1310 during the return stroke. The pin 1221 is prevented from moving while the receiver shuttle body is allowed to continue moving in its vertical path. This creates a relative motion between the sliding rack 1210 and the receiving pinion screw 1230 which in turn releases the distal end of the needle 101. The relative motion of the rack 1210 continues until the rack bottoms out in its cavity in the receiver shuttle assembly 1200. When this happens, the ratchet 1320 is over-come by the rack 1210 at its full travel or when the ratchet is manually disengaged by the user.

FIGS. 14-17 thus show an alternative shuttle mechanism for grasping the needle 101 both before and after the needle passes through the tissue to complete a suturing operation. The shuttle mechanism in this alternative embodiment is an active mechanism that captures the needle after it passes through the tissue as shown in the figures. The pinion screws 1241, 1230 represent needle gripping elements and rotation thereof causes either release or capture of the suturing needle. These needle gripping elements thus include different positions including a needle receiving position and a needle gripping position.

Similar to the device 100, the device 1100 utilizes wrist motion of the user to advance the needle initially into and through the tissue as shown in FIGS. 14-17.

In accordance with the embodiment of FIGS. 14-17, a device for suturing tissue includes a handle and a suturing needle having a first pointed end and an opposite second end. The device includes an actuator and a linkage for operatively connecting the actuator to a needle transfer mechanism that is configured to transfer the suturing needle between an initial first (home) position in which the suturing needle is grasped and positioned for advancement into and through the tissue and a second position in which the suturing needle is grasped by a moveable shuttle body and actively extracted from the tissue. The needle transfer mechanism is of a reversible type (similar to device 100) to allow the needle to be transferred back to the first position from the second position. The shuttle body moves according to at least two distinct phases, namely, a first phase in which the shuttle body moves exclusively in an axial direction (e.g., along a longitudinal axis of the handle) and a second phase in which the shuttle body rotates, wherein the shuttle body grips the suturing needle prior to its rotation which causes extraction of the suturing needle from the tissue. The shuttle body moves according to both the first and second phases in one actuator cycle (i.e., depressing the actuator body once) and thus, the extraction of the needle (by the shuttle body moving to the second position) is effectuated directly by motion of the actuator body.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A device for suturing tissue comprising:
   a handle;
   a suturing needle having a first pointed end and an opposite second end;
   a first needle gripper coupled to the handle, the first needle gripper having an open position in which the suturing needle can freely move relative thereto and a closed position in which the suturing needle is held by the first needle gripper, the first needle gripper having a base part and a movable part that moves relative to the base part;
   a second needle gripper coupled to the handle, the second needle gripper being movable relative to the handle and having an open position in which the suturing needle can freely move relative thereto and a closed position in which in the suturing needle is held by the second needle gripper, the second needle gripper being rotatable about a first axis, the second needle gripper having a base part and a moveable part that moves relative to the base part; and
   a single actuator that is operatively coupled to the second needle gripper, wherein actuation of the single actuator: (1) rotates the second needle gripper relative to the handle, and (2) acts on the first needle gripper to cause the movable part of the first needle gripper to move relative to the base part and assume one of the open and closed positions and acts on the second needle gripper to cause the movable part of the second needle gripper to move relative to the base part and assume the other of the open and closed positions;
   wherein prior to insertion of the suturing needle into the tissue, the suturing needle is held by the first needle gripper and subsequent to passage of the suturing needle through the tissue and upon activation of the single actuator, the suturing needle is released from the first needle gripper and is captured and held by the second needle gripper to allow retraction of the suturing needle from the tissue.

2. The device of claim 1, wherein the suturing needle is held by at least one of the first and second grippers at all times and the second needle gripper is at least partially surrounded by a safety mechanism in that the second needle gripper pivotally travels within an interior space defined by a frame of the safety mechanism, the safety mechanism being coupled to the handle for shielding the first pointed end of the suturing needle.

3. The device of claim 1, wherein the first needle gripper is fixedly attached to the handle, wherein rotation of the second needle gripper in a first direction towards the tissue allows capture of the suturing needle after the suturing needle exits the tissue and subsequent rotation of the second needle gripper about the first axis in an opposite second direction away from the tissue causes retraction of the suturing needle from the tissue, the handle being rotatable about the first axis.

4. The device of claim 3, wherein each of the first and second needle grippers includes a biased pin member that moves in a reciprocating manner between the open and closed positions and intimately engages the suturing needle in the closed position resulting in the suturing needle being held by the respective needle gripper.

5. The device of claim 3, wherein the single actuator and the first and second needle grippers are configured such that subsequent activation of the single actuator, after the suturing needle has been captured by the second needle gripper, causes rotation of the second needle gripper back in the first direction to effectuate transfer of the suturing needle from the second needle gripper back to the first needle gripper, thereby allowing the suturing needle to be again driven into and through the tissue.

6. The device of claim 5, wherein during transfer of the suturing needle from the second needle gripper to the first needle gripper, the second needle gripper assumes the open position and the first needle gripper assumes the closed position causing the suturing needle to be held by the first needle gripper.

7. The device of claim 1, further including a safety mechanism coupled to the handle and configured for shielding the first pointed end of the suturing needle, wherein activation of the single actuator causes each of the first and second needle grippers to move in a reciprocating manner between the open and closed positions and causes the second needle gripper to rotate about the first axis to a needle transfer position.

8. The device of claim 7, wherein the safety mechanism is rotatable about the first axis, the rotation of the safety mechanism being independent from rotation of the second needle gripper about the same first axis.

9. The device of claim 8, wherein the safety mechanism comprises a spring biased shield that is spaced from the second needle gripper and shrouds the suturing needle during needle penetration and when the suturing needle exits the tissue, the shield being rotatable about the first axis, wherein the shield comprises a first shield member and a second shield member spaced from the first shield member.

10. The device of claim 9, wherein at least one of the first and second shield members includes an alignment feature for indicating to a user a location at which the first pointed end of the suturing needle passes through the respective shield, the alignment feature including alignment indicia that defines the location.

11. The device of claim 1, further including a lockout mechanism including a lockout deactivating element for deactivating the lockout mechanism, a lockout element and means to connect the single actuator element to the lockout element, wherein the lockout element is configured to prevent a safety mechanism, which is coupled to the handle, from exposing the first pointed end until the lockout mechanism is deactivated.

12. The device of claim 1, further including a suture cutter disposed within one of the handle and the actuator, the cutter including a slideable blade, an actuator, and a notch to align the suture for cutting.

13. The device of claim 1, wherein the handle is configured to rotate about an axle that defines the first axis such that prior to insertion of the suturing needle into the tissue, the handle is positioned at a first acute angle relative to a tissue surface and the device is configured such that rotation of the handle about the first axis to a different position, in which the handle is positioned at a second acute angle relative the tissue surface, causes the suturing needle to be manually driven into and through the tissue and permits capture of the first pointed end by the second needle gripper upon activation of the single actuator.

14. The device of claim 13, wherein successive activations of the actuator cause rotation of the second needle gripper about the first axis and depending upon an operating state of the second needle gripper either causes capture of the suturing needle by the second needle gripper or release of the suturing needle by the second needle gripper to allow capture of the suturing needle by the first needle gripper and permit return of the suturing needle to the first needle gripper, thereby allowing the suturing needle to be again driven into the tissue.

15. The device of claim 1, further including a drive assembly for moving the second needle gripper about the first axis and causing the first and second needle grippers to move between the open and closed positions, the drive assembly including a cam shaft, the rotation of which causes the first and second needle grippers to assume one of the open and closed positions, the drive assembly being operatively coupled to the single actuator, whereby activation of the single actuator is translated into rotation of the cam shaft.

16. The device of claim 1, wherein the single actuator is operatively coupled to a drive assembly that has a rotatable component that is configured such that rotation of the rotatable component is translated into the first needle gripper assuming one of the open and closed positions and the second needle gripper assuming the other of the open and closed positions.

17. The device of claim 16, wherein the rotatable component comprises a cam shaft that contacts the first and second needle grippers in an alternating manner.

18. The device of claim 1, wherein the second needle gripper rotates about the first axis between a fully retracted position and a fully extended position, wherein in the fully retracted position, a distal end of the second needle gripper is at least partially contained within the handle.

19. The device of claim 1, wherein the single actuator is configured such that during an instroke of the actuator, the second needle gripper rotates about the first axis between a fully retracted position and a fully extended position and each of the first and second needle grippers assumes one of the open and closed positions.

20. The device of claim 1, wherein the single actuator is operatively connected to: (1) a first linkage for controlling rotation of the second needle gripper about the first axis between a fully retracted position and a fully extended position and (2) a second linkage for altering a state of each of the first and second needle grippers between the open and closed positions.

21. A device for suturing tissue comprising:
a handle;
a suturing needle having a first pointed end and an opposite second end;
a first needle gripper coupled to the handle, the first needle gripper having an open position in which the suturing needle can freely move relative thereto and a closed position in which the suturing needle is held by the first needle gripper;
a second needle gripper coupled to the handle, the second needle gripper being movable relative to the handle and having an open position in which the suturing needle can freely move relative thereto and a closed position in which in the suturing needle is held by the second needle gripper, the second needle gripper being rotatable about a first axis; and
a single actuator that is operatively coupled to the second needle gripper by a first linkage, wherein actuation of the single actuator rotates the second needle gripper relative to the handle, and wherein the single actuator is operatively coupled to the first needle gripper and the second needle gripper by a second linkage and the single actuator is also configured such that the actuation of the single actuator causes the first needle gripper to assume one of the open and closed positions as a result of a movable part of the first needle gripper moving relative to a base portion of the first needle gripper and to cause the second needle gripper to assume the other of the open and closed positions as a result of a movable part of the second needle gripper moving relative to a base portion of the second needle gripper, the second linkage being different than the first linkage;
wherein prior to insertion of the suturing needle into the tissue, the suturing needle is held by the first needle gripper and subsequent to passage of the suturing needle through the tissue and upon activation of the single actuator, the suturing needle is released from the first needle gripper and is captured and held by the second needle gripper to allow retraction of the suturing needle from the tissue.

* * * * *